United States Patent
Deguchi et al.

(10) Patent No.: US 6,852,744 B2
(45) Date of Patent: Feb. 8, 2005

(54) PYRROLIDINE DERIVATIVES AND THEIR USE AS CHYMASE INHIBITOR

(75) Inventors: Takashi Deguchi, Kobe (JP); Ryotaro Shiratake, Osaka (JP); Fuminori Sato, Kobe (JP); Buichi Fujitani, Sakai (JP); Yayoi Honda, Ibaraki (JP); Akihiko Kiyoshi, Kobe (JP); Mitsue Notake, Suita (JP); Graham Andrew Showell, Lackford (GB); Robert George Boyle, Cambridge (GB); Sukhbinder Singh Klair, Linton (GB)

(73) Assignee: Dainippon Pharmaceutical Co., Ltd., Osaka-Fu (JP)

( * ) Notice: Subject to any disclaimer, the term of this patent is extended or adjusted under 35 U.S.C. 154(b) by 156 days.

(21) Appl. No.: 10/363,036

(22) PCT Filed: Aug. 21, 2001

(86) PCT No.: PCT/JP01/07137

§ 371 (c)(1),
(2), (4) Date: Feb. 28, 2003

(87) PCT Pub. No.: WO02/18378

PCT Pub. Date: Mar. 7, 2002

(65) Prior Publication Data

US 2004/0102384 A1 May 27, 2004

(30) Foreign Application Priority Data

Aug. 30, 2000 (GB) .............................. 0021315

(51) Int. Cl.[7] .................. A61K 31/42; A61K 31/41; C07D 261/18; C07D 285/06

(52) U.S. Cl. ..................... 514/378; 514/361; 548/248; 548/127

(58) Field of Search ................ 548/248, 127; 514/378, 361

(56) References Cited

FOREIGN PATENT DOCUMENTS

| WO | 93/25574 | 12/1993 |
|---|---|---|
| WO | 00/52032 | 9/2000 |

OTHER PUBLICATIONS

Patent Abstracts of Japan, vol. 1997, no. 09, Sep. 30, 1997 & JP 09 124691 A (Green Cross Corp: The), May 13, 1997, abstract.

Patent Abstracts of Japan, vol. 1998, no. 06, Apr. 30, 1998 & JP 10 053579 (Fujisawa Pharmaceut Co Ltd) Feb. 24, 1998, abstract.

Primary Examiner—Deborah C. Lambkin
(74) Attorney, Agent, or Firm—Wenderoth, Lind & Ponack, L.L.P.

(57) ABSTRACT

Novel pyrrolidine derivatives, being useful as chymase inhibitor or intermediate for synthesis of the active compounds, which has the formula (I): wherein $R^1$ is cycloalkyl, substituted or unsubstituted phenyl or naphthyl, indanyl, thienyl, furyl, substituted or unsubstituted indolyl, benzofuryl, substituted or unsubstituted benzothienyl, etc.; $R^2$ is H, alkyl, phenyl-lower alkyl, cycloalkyl or cycloalkyl-lower alkyl; $R^3$ is (i) substituted or unsubstituted monocyclic heterocyclic group, (ii) substituted or unsubstituted benzene- or pyridine-fused heterocyclic group, or (iii) a group (a): $R^4$ and $R^5$ are independently H or OH, but $R^4$ and $R^5$ are not simultaneously H, or both form oxo; n is 0, 1, 2 or 3; or a salt thereof.

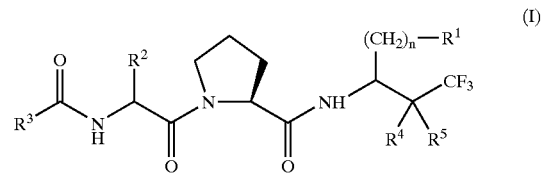

(I)

45 Claims, No Drawings

PYRROLIDINE DERIVATIVES AND THEIR USE AS CHYMASE INHIBITOR

TECHNICAL FIELD

This invention relates to pyrrolidine derivatives useful as a chymase inhibitor and intermediates for the synthesis thereof.

BACKGROUND ART

Chymase, a chymotrypsin-like serine protease discovered in 1975, is released upon mast cell degranulation. Although it is known that chymase is able to cleave extracellular matrix and other biologically active substances, much attention has been given to its ability to convert angiotensin I, in a manner independent of that of angiotensin-converting enzyme, to the vasoconstrictor angiotensin II. Previous studies have suggested that the formation of angiotensin II within the human heart is mainly controlled by chymase rather than by angiotensin-converting enzyme [Circ. Res. 66, 883–890 (1990)]. Accordingly, it has been assumed that chymase plays an important role in the progression of cardiovascular diseases such as cardiac hypertrophy, myocardial infarction, vascular hyperplasia, and restenosis following angioplasty.

Moreover, it has been shown that chymase enhances histamine release from mast cells and induces a prolonged increase in microvascular permeability independent of histamine [Eur. J. Pharmacol. 352, 91–98 (1998)]. It is, therefore, highly possible that chymase plays an important role, not only in the immediate type of allergic inflammatory reactions, but also in the delayed ones, which are known to involve mast cells.

Mast cells containing chymase as well as tryptase are mainly distributed in connective tissues, while those containing tryptase, but not chymase, are mainly present in mucosal tissues. In addition, it has been reported that chymase activity increases significantly with the progression of tissue fibrosis including intraperitoneal adhesion formation [FEBS Letters 406, 301–304 (1997), J. Surg. Res. 92, 40–44 (2000)]. These findings indicate that chymase may participate in tissue fibrosis.

In addition to its possible involvement in a range of diseases and complications, chymase is known to have various other physiological activities such as, formation of other active proteases for matrix degradation, activation of the inflammatory cytokine IL-1 β precursor, formation of the active TGF-β in fibrosis, enhancement of foam cell formation and maintenance in atherogenesis, and conversion of big endothelins to contractile 31-amino acid length endothelins. Accordingly, it is suggested that chymase may play an important role in blood flow regulation, allergy, inflammation, and tissue remodeling. Combining the information above, it is expected that chymase inhibitors, acting as antiallergic, antiinflammatory, antirestenotic, or antiarteriosclerotic agents, may provide novel treatments for a wide range of diseases and complications.

Studies have hitherto been made for finding an excellent chymase inhibitor, and there are reported various kinds of chymase inhibitors, for example, it is disclosed in WO-A-93/25574 that a wide range of compounds have a chymase inhibitory activity, but no specific data of the activity is disclosed. WO-A-93/25574 includes very broad claims and discloses 28 examples, among which the compound of Example 21 has the following formula (A):

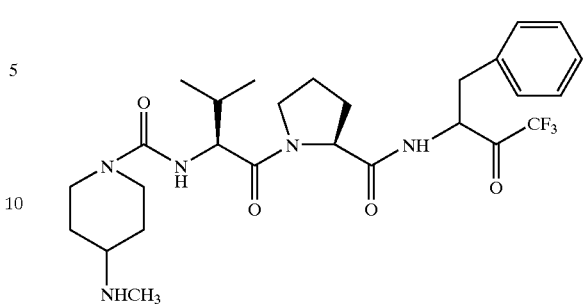

In the following formula (I) of the present compounds, the above compound (A) is not includes. That is, $R^3$ of the following formula (I) means an unsaturated monocyclic heterocyclic group, but not a saturated monocyclic heterocyclic group. In addition, as disclosed in Experiments as described below, the chymase inhibitory activity of the compound (A) is far weaker than that of the present compounds.

DISCLOSURE OF INVENTION

An object of the present invention is to provide novel pyrrolidine derivatives having a chymase inhibitory activity. Another object of the invention is to provide a pharmaceutical composition comprising as an active ingredient said novel pyrrolidine derivative in admixture with a pharmaceutically acceptable carrier or diluent. A further object of the invention is to provide a chymase inhibitory agent.

A pyrrolidine derivative of the present invention has the following formula (I):

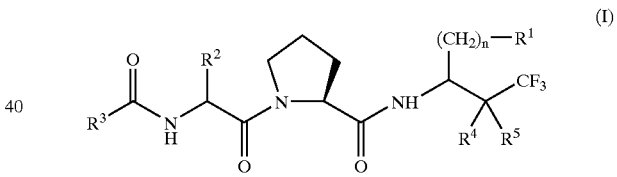

wherein $R^1$ is a cycloalkyl group, a substituted or unsubstituted phenyl group, a substituted or unsubstituted naphthyl group, a tetrahydronaphthyl group, an indanyl group, a thienyl group, a furyl group, a substituted or unsubstituted indolyl group, a substituted or unsubstituted dihydroindolyl group, a benzofuryl group, a dihydrobenzofuryl group, a substituted or unsubstituted benzothienyl group or an S-mono- or di-oxide thereof, or a dihydrobenzothienyl group, said substituted phenyl, naphthyl and benzothienyl groups having each independently one to three substituents independently selected from a halogen atom, a lower alkoxy group, a hydroxy group and a lower alkyl group having optionally one to three halogen atoms; and said substituted indolyl and dihydroindolyl groups having a substituent on (N) at the 1-position selected from a lower alkyl group and a lower alkyl-carbonyl group;

$R^2$ is a hydrogen atom, an alkyl group, a phenyl-lower alkyl group, a cycloalkyl group or a cycloalkyl-lower alkyl group;

$R^3$ is (i) a substituted or unsubstituted, unsaturated monocyclic heterocyclic group;

(ii) a substituted or unsubstituted, saturated or unsaturated monocyclic heterocyclic group which is fused by a benzene ring or a pyridine ring, wherein said substituted heterocyclic groups in (i) and (ii) each independently have one to three substituents independently selected from a halogen atom, a lower alkyl group, a lower alkoxy group, a lower alkyl-carbonyl group, a cyano group, a carboxamido group, a phenyl group and a phenoxy group; said phenyl and phenoxy substituents may further optionally have one to three substituents independently selected from a halogen atom, a lower alkyl group and a halogeno-lower alkyl group; or (iii) a group of the formula (a):

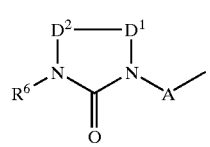

(a)

wherein A is a lower alkylene group, $D^1$ and $D^2$ are both simultaneously a methylene group (—$CH_2$—) or alternatively, one of $D^1$ and $D^2$ is a methylene group (—$CH_2$—) and another is a vinylene group (—CH=CH—) where each methylene group being optionally substituted by an oxo group or a lower alkyl group, and said vinylene group being optionally substituted by a lower alkyl group; $R^6$ is a lower alkyl group substituted by a carboxyl group, a lower alkoxycarbonyl group or a phenyl group;

$R^4$ and $R^5$ are each independently a hydrogen atom or a hydroxy group, but $R^4$ and $R^5$ are not simultaneously a hydrogen atom, or both combines to form an oxo group;

n is 0, 1, 2 or 3;

or a salt thereof.

Throughout the description and claims, the term "lower alkyl group" or "lower alkyl" moiety denotes a straight chain and branched alkyl group having 1 to 6 carbon atoms, and includes, for example, methyl, ethyl, propyl, isopropyl, butyl, tert-butyl, pentyl, and hexyl.

The term "lower alkoxy group" denotes a straight chain or branched chain alkoxy group having 1 to 6 carbon atoms, and includes, for example, methoxy, ethoxy, propoxy, isopropyloxy, butoxy, pentyloxy, and hexyloxy.

The "cycloalkyl group" denotes a cycloalkyl group having 3 to 8 carbon atoms, and includes, for example, cyclopropyl, cyclobutyl, cyclopentyl, cyclohexyl, cycloheptyl, and cyclooctyl.

The term "lower alkylene group" denotes a straight chain or branched chain alkylene group having 1 to 6 carbon atoms, and includes, for example, methylene, ethylene, propylene, butylene, isobutylene, pentylene, and hexylene.

The "lower alkyl-carbonyl group" denotes a carbonyl group substituted by a straight chain or branched chain alkyl having 1 to 6 carbon atoms, and includes, for example, acetyl, propionyl, butyryl, pentanoyl, and hexanoyl.

The "halogen atom" denotes fluorine atom, bromine atom, chlorine atom, or iodine atom.

The "unsaturated monocyclic heterocyclic group" for $R^3$ denotes an unsaturated 5- to 7-membered, preferably 5- or 6-membered, monocyclic heterocyclic group containing one to three heteroatoms selected from nitrogen atom, oxygen atom and sulfur atom, and includes, for example, furyl, thienyl, oxazolyl, isoxazolyl, thiazolyl, isothiazolyl, 1,2,3-thiadiazolyl, 1,2,4-oxadiazolyl, and pyridyl.

The "saturated or unsaturated monocyclic heterocyclic group which is fused by a benzene ring or a pyridine ring" for $R^3$ denotes a saturated or unsaturated 5- to 7-membered, preferably 5- or 6-membered, monocyclic heterocyclic group containing one to three heteroatoms selected from nitrogen atom, oxygen atom and sulfur atom which is fused by a benzene ring or a pyridine ring, and includes, for example, benzofuryl, benzothienyl, indolyl, benzoxazolyl, benzisoxazolyl, benzothiazolyl, benzisothiazolyl, benzofurazanyl or N-oxide thereof, quinolyl, benzodioxolyl, and isoxazolo[4,3-b]pyridinyl.

The group of the formula (a) for $R^3$ includes, for example, the groups of the following formulae:

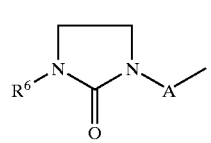

(a-1)

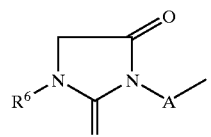

(a-2)

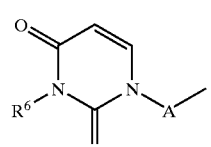

(a-3)

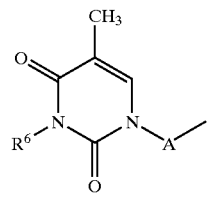

(a-4)

wherein A and $R^6$ are as defined above.

Preferred compounds of the present invention are the compounds of the formula (I) wherein $R^1$ is a $C_3$–$C_8$ cycloalkyl group, a phenyl group, a phenyl substituted by one to three substituents independently selected from a halogen atom, a $C_1$–$C_4$ alkoxy group, a hydroxy group, a $C_1$–$C_4$ alkyl group and a halogeno-$C_1$–$C_4$ alkyl group; a naphthyl group, a tetrahydronaphthyl group, an indanyl group, a thienyl group, a furyl group, an indolyl group, an N—($C_1$–$C_4$ alkyl)indolyl group, an N—($C_1$–$C_4$ alkylcarbonyl)indolyl group, a dihydroindolyl group, a benzofuryl group, a dihydrobenzofuryl group, a benzothienyl group or an S-mono- or di-oxide thereof, or a dihydrobenzothienyl group;

$R^2$ is a hydrogen atom, a $C_1$–$C_6$ alkyl group, a phenyl-$C_1$–$C_4$ alkyl group, a $C_3$–$C_8$ cycloalkyl group or a $C_3$–$C_8$ cycloalkyl-$C_1$–$C_4$ alkyl group;

$R^3$ is (i) an unsaturated monocyclic heterocyclic group selected from furyl, thienyl, oxazolyl, isoxazolyl, thiazolyl, isothiazolyl, 1,2,3-thiadiazolyl, 1,2,4-oxadiazolyl, and pyridyl;

(ii) a benzene- or pyridine-fused saturated or unsaturated monocyclic heterocyclic group selected from benzofuryl, benzothienyl, indolyl, benzoxazolyl, benzisoxazolyl, benzothiazolyl, benzisothiazolyl, benzofurazanyl or N-oxide thereof, quinolyl, benzodioxolyl, and isoxazolo[4,3-b]pyridinyl, wherein said heterocyclic groups in (i) and (ii) may each independently have one to three substituents independently selected from a fluorine or chlorine atom, a $C_1$–$C_4$ alkyl group, a $C_1$–$C_4$ alkoxy group, a $C_1$–$C_4$ alkyl-carbonyl group, a cyano group, a carboxamido group, a phenyl group and a phenoxy group; said phenyl and phenoxy substituents may further optionally have one to three substituents independently selected from a halogen atom, a $C_1$–$C_4$ alkyl group and a halogeno-$C_1$–$C_4$ alkyl group; or (iii) a group of any one of the formulae (a-1) to (a-4):

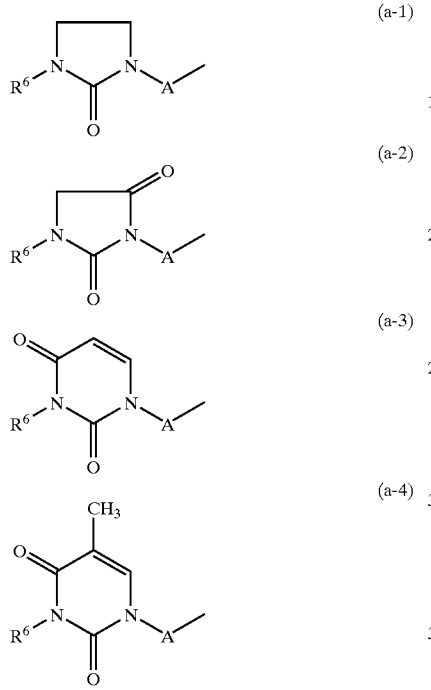

wherein A is a $C_1$–$C_4$ alkylene group, and $R^6$ is a $C_1$–$C_4$ alkyl group substituted by a carboxyl group, a $C_1$–$C_5$ alkoxycarbonyl group or a phenyl group;

$R^4$ and $R^5$ are each independently a hydrogen atom or a hydroxy group but $R^4$ and $R^5$ are not simultaneously a hydrogen atom, or both combines to form an oxo group;

n is 1 or 2;

or a salt thereof.

More preferred compounds of the present invention are the compounds of the formula (I) wherein $R^1$ is a $C_5$–$C_7$ cycloalkyl group, a phenyl group, a phenyl group substituted by one to three substituents independently selected from fluorine, chlorine or bromine atom, a $C_1$–$C_4$ alkoxy group, a hydroxy group, a $C_1$–$C_4$ alkyl group and a trifluoromethyl group; a naphthyl group, a tetrahydronaphthyl group, an indanyl group, a thienyl group, a furyl group, an indolyl group, an N—($C_1$–$C_4$ alkyl)indolyl group, an N-acetylindolyl group, a dihydroindolyl group, a benzofuryl group, a dihydrobenzofuryl group, a benzothienyl group or an S-mono- or di-oxide thereof, or a dihydrobenzothienyl group;

$R^2$ is a hydrogen atom, a $C_1$–$C_4$ alkyl group, a phenyl-$C_1$–$C_2$ alkyl group, a $C_5$–$C_7$ cycloalkyl group or a $C_5$–$C_7$ cycloalkyl-$C_1$–$C_2$ alkyl group;

$R^3$ is (i) an unsaturated monocyclic heterocyclic group selected from furyl, thienyl, oxazolyl, isoxazolyl, thiazolyl, isothiazolyl, 1,2,3-thiadiazolyl, 1,2,4-oxadiazolyl, and pyridyl;

(ii) a benzene- or pyridine-fused saturated or unsaturated monocyclic heterocyclic group selected from benzoxazolyl, benzisoxazolyl, benzofurazanyl or N-oxide thereof, quinolyl, benzodioxolyl, and isoxazolo[4,3-b]pyridinyl, wherein said heterocyclic groups in (i) and (ii) may each independently have one to three substituents independently selected from the group consisting of a fluorine or chlorine atom, a $C_1$–$C_3$ alkyl group, a $C_1$–$C_3$ alkoxy group, an acetyl group, a cyano group, a carboxamido group, a phenyl group and a phenoxy group, said phenyl and phenoxy substituents may further optionally have one to three substituents selected from a fluorine or chlorine atom, a $C_1$–$C_3$ alkyl group and a trifluoromethyl group; or (iii) a group of any one of the formulae (a-1) to (a-4):

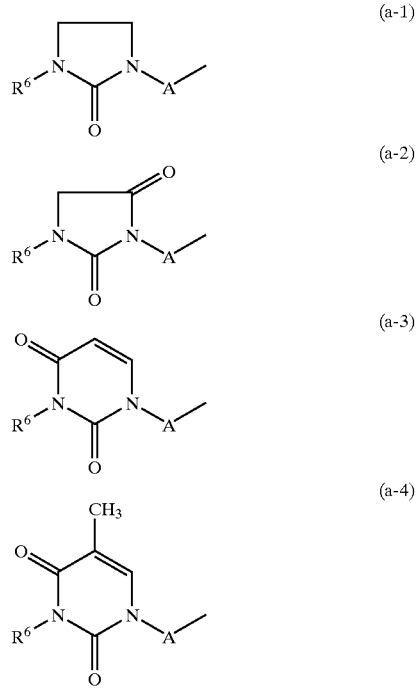

wherein A is a $C_1$–$C_2$ alkylene group, and $R^6$ is a $C_1$–$C_2$ alkyl group substituted by a carboxyl group, a tert-butoxycarbonyl group or a phenyl group;

$R^4$ and $R^5$ are each independently a hydrogen atom or a hydroxy group, but $R^4$ and $R^5$ are not simultaneously a hydrogen atom, or both combines to form an oxo group;

n is 1 or 2;

or a salt thereof.

The compounds (I) of the present invention may be classified into two groups by the kinds of $R^4$ and $R^5$ groups, that is, when the $R^4$ and $R^5$ groups combine to form an oxo group, the compounds are shown by the following formula (I-A), and when one of the $R^4$ and $R^5$ groups is a hydrogen atom and another is a hydroxy group, the compounds are shown by the following formula (I-B).

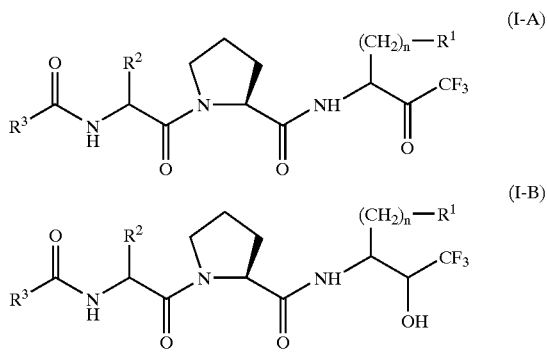

wherein $R^1$, $R^2$, $R^3$ and n are as defined above.

The compound of the formula (I-A) may have a structure wherein the keto group for the corresponding $R^4$ and $R^5$ in the formula (I) is converted into two hydroxy groups by addition of a water molecule.

The compounds of the formula (I-A) have excellent chymase inhibitory activity and hence are useful as a medicament. The compounds of the formula (I-B) can be converted into the compounds of the formula (I-A) by oxidizing them, and hence are useful as an intermediate for preparing the active compounds (I-A).

The compounds of the formula (I-A) have high blood level by oral administration to exhibit excellent chymase inhibitory activity. The characteristic properties of the compounds (I-A) may due to the kinds of substituents of $R^3$, particularly a combination of said $R^3$ with other substituents, such as $R^1$ and others.

In view of the excellent chymase inhibitory activity, particularly preferred compounds are compounds of the formula (I-A'):

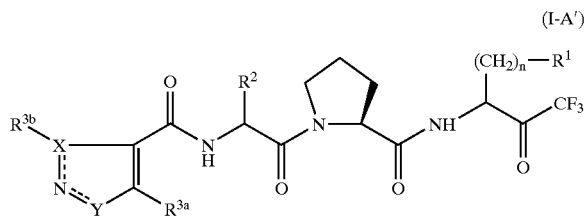

wherein $R^{3a}$ and $R^{3b}$ are independently a hydrogen atom, a lower alkyl group, a lower alkyl-carbonyl group, or a phenyl group which may be substituted by a halogen atom or a halogeno-lower alkyl group; X is a carbon atom or a sulfur atom; Y is an oxygen atom or a nitrogen atom; and the symbol ═══ means a single bond or double bond, and $R^1$, $R^2$ and n are as defined above, or a pharmaceutically acceptable salt thereof.

Among the preferred compounds (I-A'), especially preferred compounds are the compounds of the formula (I-A') wherein X is a carbon atom and Y is an oxygen atom, or X is a sulfur atom and Y is a nitrogen atom, and other symbols are as defined above, or a pharmaceutically acceptable salt thereof. In an especially preferred compounds of the formula (I-A'), wherein $R^1$ is a substituted or unsubstituted phenyl group, a substituted or unsubstituted naphthyl group or a benzothienyl group, said substituted phenyl group and substituted naphthyl group have each independently one to three substituents independently selected from a halogen atom, a methyl group, a methoxy group, a trifluoromethyl group and a hydroxy group.

BEST MODE FOR CARRYING OUT THE INVENTION

Suitable compounds of the formula (I-A') are exemplified below.

Compound 1-A-1:

N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-(methylethyl)-2-oxoethyl](3,5-dimethylisoxazol-4-yl)carboxamide;

Compound 1-A-2:

N-[(1S)-2-((2S)-2-{N-[(1S)-3,3,3-trifluoro-1-(2-naphthylmethyl)-2-oxopropyl]carbamoyl}pyrrolidinyl)-1-(methylethyl)-2-oxoethyl](3,5-dimethylisoxazol-4-yl)carboxamide;

Compound 1-A-3:

N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-ethyl-2-oxoethyl](3,5-dimethylisoxazol-4-yl)carboxamide;

Compound 1-A-4:

N-[1-((1R)-1-methylpropyl)(1S)-2-((2S)-2-{N-[(1S)-1-(benzo[b]thiophen-3-ylmethyl)-3,3,3-trifluoro-2-oxopropyl]carbamoyl}pyrrolidinyl)-2-oxoethyl](3,5-dimethylisoxazol-4-yl)carboxamide;

Compound 1-A-5:

N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-methyl-2-oxoethyl](3,5-dimethylisoxazol-4-yl)carboxamide;

Compound 1-A-20:

N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-(methylethyl)-2-oxoethyl](4-methyl(1,2,3-thiadiazol-5-yl))carboxamide;

The compounds (I) of the present invention have several asymmetric carbons and include enantiomers, diastereomers and mixtures thereof. These isomers and mixtures thereof are also included in the present invention. Further, the compounds (I) may be in the form of a hydrate and/or a salt, which are also included in the present invention. The salts of the compounds of the formula (I) are not limited to any specific one but are preferably pharmaceutically acceptable salts, for example, a salt with an organic base (e.g. trimethylamine, triethylamine, N-methylmorpholine), a salt with an inorganic metal (e.g. sodium, potassium). Some compounds of the formula (I) may form an acid addition salt with an organic acid such as tartaric acid, fumaric acid, acetic acid, lactic acid, succinic acid, methanesulfonic acid, maleic acid, malonic acid, gluconic acid, an amino acid (e.g. aspartic acid), or with an inorganic acid (e.g. hydrochloric acid, phosphoric acid).

Processes for the Preparation of the Compounds (I)

The compounds (I) of the present invention are prepared by the processes as mentioned below.

One preferred process is shown by the following Reaction Scheme-1.

Reaction Scheme-1

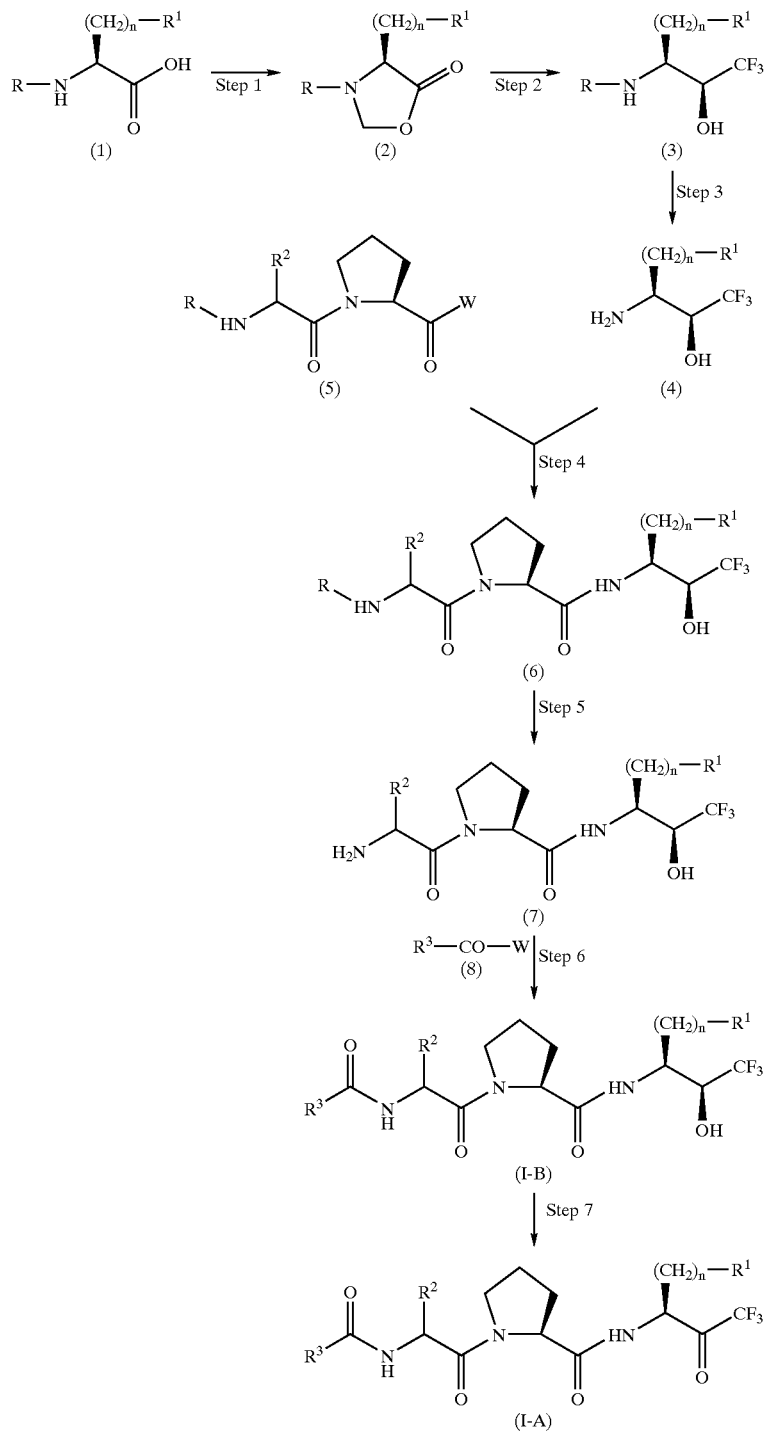

wherein R is a protecting group for an amino group and W is a leaving group, and $R^1$, $R^2$, $R^3$ and n are as defined above.

The protecting group for an amino group defined by R is inclusive any conventional amino-protecting groups, for example, alkoxycarbonyl groups (e.g. tert-butoxycarbonyl, abbreviated as "Boc") which can be removed by hydrolysis with an acid or a base, or substituted or unsubstituted benzyloxycarbonyl groups (which are usually indicated by the symbol "Z") which can be removed by hydrogenolysis.

The leaving group defined by "W" in the above reaction includes a hydroxy group, a halogen atom, a lower alkoxy group, a lower alkylthio group, a lower alkylsulfinyl group, or a lower alkylsulfonyl group.

In the above Reaction Scheme-1, Step 1, a known compound (1) is treated with paraformaldehyde to give the compound (2). In Step 2, the compound (2) is converted into the compound (3) by reacting it with a tri(lower alkyl) trifluoromethyl)silane compound (e.g., trimethyl (trifluoromethyl)silane) in the presence of cesium fluoride, treating the reaction product with methanol, reducing the resulting product to make ring-opening and then de-hydroxymethylating. The reduction for ring-opening is usually carried out with sodium borohydride, and the de-hydroxymethylation is carried out by treating with a base such as potassium carbonate. In Step 3, the amino-protecting group "R" of the compound (3) is removed by a conventional method as mentioned above to give the compound (4). The reaction in these steps 1, 2 and 3 may be done step by step or alternatively by one-pot reaction.

In Step 4, the compound (4) obtained above is reacted with a known compound (5). The reaction in this step is carried out by a conventional amidation reaction which is usually used for production of peptides. For instance, the compound (4) is reacted with the compound (5) by mixing them in a solvent (e.g. methylene chloride, dimethylformamide) or without solvent and stirring the mixture in the presence or absence of a base (e.g. triethylamine) at room temperature or at an elevated temperature. When the symbol "W" of the compound (5) is a hydroxy group, the reaction in Step 4 is advantageously carried out in the presence of a condensation agent, such as 1-ethyl-3-(3-dimethylaminopropyl)carbodiimide, N,N'-dicyclohexylcarbodiimide, 1,1'-carbonyldiimidazole, or N,N'-disuccinimidyl carbonate. When the symbol "W" is a hydroxy group, the reaction in Step 4 may also be carried out by firstly reacting the compound (5) with ethyl chloroformate in the presence of a tertiary amine such as triethylamine or preferably N-methylmorpholine, followed by reacting the resultant with the compound (4).

In Step 5, the amino-protecting group "R" of the compound (6) is removed by a conventional method. For example, when the amino-protecting group is tert-butoxycarbonyl, it is removed by contacting the compound (6) with an acid, such as trifluoroacetic acid, hydrochloric acid, hydrobromic acid, sulfuric acid, or acetic acid. The reaction is carried out in a solvent, such as methylene chloride, ethyl acetate, tetrahydrofuran, benzene, toluene, or a mixture of them. When the amino-protecting group "R" in the compound (6) is a benzyloxycarbonyl group, the removal thereof can be advantageously carried out by treating the compound (6) with hydrogen gas in a solvent (e.g. ethyl acetate, ethanol) in the presence of a catalyst (e.g. platinum, palladium, Raney nickel) at a temperature of lower than 60° C., usually at room temperature.

The thus-prepared compound (7) is then reacted with the compound (8) in Step 6. The reaction is carried out in the same manner as in Step 4 to give the compound (I-B). The compound (8) is novel when the symbol "$R^3$" is a group of the formula (a), and said compound can be prepared by the process as described hereinafter in Reference Examples or in a similar manner. When the symbol "$R^3$" is a group other than the formula (a), the compound (8) is known, among which the compound of the following formula (II) is particularly important.

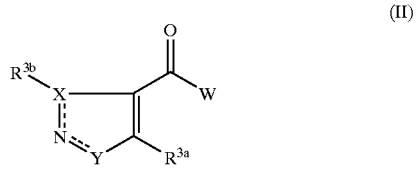

(II)

wherein $R^{3a}$, $R^{3b}$, X, Y, W and the symbol ═══ are as defined above. Although the compounds of the above formula (II) are known, they have never been used for the preparation of the compounds of the formula (I-A) of the present invention.

The compounds of the formula (I-B) as prepared in the above Step 6 are novel and are useful as an intermediate for preparing the desired compounds of the formula (I-A) of the present invention which have excellent chymase inhibitory activity.

That is, in Step 7, the compound (I-B) (OH-compound) is converted into the compound (I-A) (ketone compound) by oxidizing the OH group thereof. The oxidizing reaction in Step 7 can be carried out by treating the compound (I-B) with an oxidizing agent in a solvent (e.g. methylene chloride, dimethylformamide, tetrahydrofuran, ethyl acetate, toluene). The oxidizing agent is, for example, Dess-Martin reagent which is an iodobenzene derivative. The oxidation may be carried out with phosphorus pentoxide in the presence of dimethylsulfoxide, with 1-ethyl-3-(3-dimethyaminopropylcarbodiimide-dichloroacetic acid in the presence of dimethyl sulfoxide, or with a combination of oxalyl chloride and triethylamine in the presence of dimethyl sulfoxide (so-called Swern oxidation).

In the above steps in Reaction Scheme-1, the compounds having a free carboxyl group may optionally be protected by a conventional protecting group (e.g. tert-butyl, benzyl), and the protecting group can be removed by a conventional method after the reaction. Besides, when the compounds prepared in each step have isomers, these isomers may be resolved by a conventional method.

EXAMPLES

The present invention is illustrated by the following Examples, Reference Examples and Experiments but should not be construed to be limited thereto.

In these examples, the following abbreviations are used.

Boc: tert-butoxycarbonyl

Ph: phenyl

Me: methyl

Et: ethyl

Z: benzyloxycarbonyl or (phenylmethoxy)carbonyl

THF: tetrahydrofuran

DMSO: dimethylsulfoxide

DMF: dimethylformamide

LSIMS: liquid secondary ion mass spectrometry $^1$H-NMR: proton nuclear magnetic resonance spectrometry APCIMS: atmospheric pressure chemical ionization spectrometry IR: infrared spectrometry Reference Example 1

Preparation of Raw Compound (8) in Reaction Scheme-1

2-(3-{[(tert-butyl)oxycarbonyl]methyl}-2-oxoimidazolidinyl)acetic acid (8a)

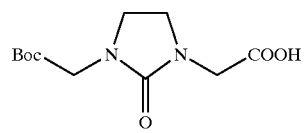

(1) To a solution of 2-oxoimidazolidine (0.3 g) and tert-butyl bromoacetate (1.50 g) in anhydrous DMF (10 ml) at 0° C.

was added lithium tert-butoxide (0.6 g). After stirring at the same temperature for 30 minutes, the reaction mixture was stirred at room temperature for 1 hour. The reaction mixture was poured into ice water and then the precipitate was collected and washed with water and dried. The precipitate was recrystallized with ethyl acetate and filtered off to give tert-butyl 2-(3-{[(tert-butyl)oxycarbonyl]methyl}-2-oxoimidazolidinyl)acetate (0.86 g) as a white solid.

m.p. 100–102° C.

LSIMS (m/z): 315[(M+H)$^+$]

$^1$H-NMR (300 MHz, CDCl$_3$): δ 1.46 (18H, s), 3.54 (4H, s), 3.89 (4H, s).

(2) To a solution of tert-butyl 2-(3-{[(tert-butyl)oxycarbonyl]methyl}-2-oxoimidazolidinyl)acetate (1.14 g) in ethanol (10 ml) and water (10 ml) was added potassium hydroxide (0.22 g) and then the reaction mixture stirred at 70° C. for 5 hours. After the ethanol was removed under reduced pressure, to the residue was added saturated aqueous sodium hydrogen carbonate solution. The aqueous phase was washed with ethyl acetate, acidified with 10% hydrochloric acid and extracted with ethyl acetate. The organic phase was dried over magnesium sulfate, filtered and evaporated under reduced pressure. The precipitate was recrystallized with ethyl acetate and filtered off to give 2-(3-{[(tert-butyl)oxycarbonyl]methyl}-2-oxoimidazolidinyl)acetic acid (0.30 g) as a colorless solid.

m.p. 112–113° C.

LSIMS (m/z): 259 [(M+H)$^+$]

$^1$H-NMR (300 MHz, CDCl$_3$): δ 1.46 (9H, s), 3.53 (4H, s), 3.89 (2H, s) 4.01 (2H, s), 7.11 (1H, br s).

Reference Example 2

Preparation of Raw Compound (8) in Reaction Scheme-1

2-(3-{[(tert-butyl)oxycarbonyl]methyl}-2,4-dioxo-1,3-dihydropyrimidinyl)acetic acid (8b)

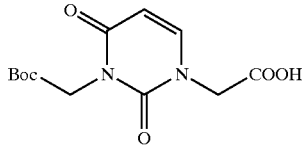

(1) To a solution of 2,4-dioxopyrimidine (1.0 g) in anhydrous DMF (10 ml) were added benzyl bromoacetate (2.5 g) and potassium carbonate (2.5 g). After stirring at room temperature for 15 hours, the reaction mixture was poured into water and extracted with ethyl acetate. The organic phase was washed with brine and then dried with magnesium sulfate, filtered and evaporated under reduced pressure. The precipitate was washed with diethyl ether to give phenylmethyl 2-(2,4-dioxo-1,3-dihydropyrimidinyl)acetate (1.4 g) as a colorless solid.

m.p. 192–194° C.

LSIMS (m/z): 261 [(M+H)$^+$]

$^1$H-NMR (300 MHz, d$_6$-DMSO): δ 4.59 (2H, s), 5.20 (2H, s), 5.62 (1H, d), 7.37 (5H, m), 7.65 (1H, d), 11.4 (1H, s).

(2) To a solution of phenylmethyl 2-(2,4-dioxo-1,3-dihydropyrimidinyl)acetate (1.0 g) in anhydrous DMF (10 ml) at 0° C. was added portionwise sodium hydride (0.18 g). After the reaction mixture was stirred for 15 minutes with cooling in an ice bath, tert-butyl bromoacetate (0.9 g) was added. After stirring the mixture at room temperature for 1 hour, to the reaction mixture was added saturated aqueous ammonium chloride solution, and the reaction mixture was extracted with ethyl acetate. The organic phase was washed with brine and dried over magnesium sulfate, filtered and evaporated under reduced pressure. The residue was purified by column chromatography (silica gel, n-hexane:ethyl acetate 2:1) to give phenylmethyl 2-(3-{[(tert-butyl)oxycarbonyl]methyl}-2,4-dioxo-1,3-dihydropyrimidinyl)acetate (1.2 g) as a colorless oil.

LSIMS (m/z):375[(M+H)$^+$]

$^1$H-NMR (300 MHz, CDCl$_3$): δ 1.46 (9H, s), 4.51 (2H, s), 4.58 (2H, s) 5.21 (2H, s), 5.81 (1H, d) 7.10 (1H, d) 7.36 (5H, m).

(3) To a solution of phenylmethyl 2-(3-{[(tert-butyl)oxycarbonyl]methyl}-2,4-dioxo-1,3-dihydropyrimidinyl)acetate (1.2) in ethyl acetate (20 ml) was added 20 wt. % palladium hydroxide (50 mg). After stirring the mixture at room temperature under a hydrogen atmosphere for 1 hour, the catalyst was removed by filtration. The filtrate was evaporated under reduced pressure to give 2-(3-{[(tert-butyl)oxycarbonyl]methyl}-2,4-dioxo-1,3-dihydropyrimidinyl)acetic acid as a white powder.

$^1$H NMR (300 MHz, CDCl$_3$): δ 1.46 (9H, s), 4.51 (2H, s), 4.59 (2H, s), 5.86 (1H, d), 7.17 (1H, d).

Reference Example 3

Preparation of Raw Compound (8) in Reaction Scheme-1

2-(2-oxo-3-benzylimidazolidinyl)acetic acid (8c)

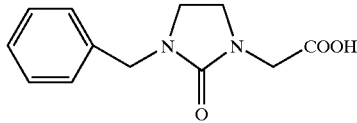

(1) To a solution of N-benzylethylenediamine (6.0 g, 40 mmol) in toluene (50 ml) at 0° C. was added 1,1'-carbonylbis-1H-imidazole (7.8 g, 48 mmol). After stirring the mixture at room temperature overnight, the reaction mixture was washed with water, 5% aqueous citric acid solution and brine. The organic phase was dried over anhydrous magnesium sulfate, filtered and evaporated under reduced pressure. The residue was recrystallized with warm ethyl acetate and filtered off to give 1-benzylimidazolidin-2-one (3.47 g).

$^1$H-NMR (300 MHz, d$_6$-DMSO): δ 7.22–7.37 (5H, m), 6.41 (1H, br s), 4.23 (2H, s), 3.14–3.26 (4H, m).

APCIMS: 177 (MH$^+$)

mp. 131–131.5° C.

(2) To a solution of 1-benzylimidazolidin-2-one (3.5 g, 19.9 mmol) in DMF (50 ml) at 0° C. were added lithium tert-butoxide (1.9 g, 23.8 mmol) and tert-butyl bromoacetate (3.2 ml, 21.8 mmol). After stirring the mixture at room temperature overnight, the reaction mixture was poured into water (100 ml) and the mixture was extracted with ethyl acetate. The organic phase was washed with water, 10% aqueous citric acid solution, saturated aqueous sodium hydrogen carbonate solution and brine. The organic solution was dried over anhydrous magnesium sulfate, filtered and evaporated under reduced pressure. The crystalline residue was washed with n-hexane, and dried to give tert-butyl 2-(2-oxo-3-benzylimidazolidinyl)acetate (5.08 g).

$^1$H-NMR (300 MHz, CDCl$_3$): δ 7.24–7.36 (5H, m), 4.40 (2H, s), 3.90 (2H, s), 3.40–3.46 (2H, m), 3.26–3.20 (2H, m).

(3) To a solution of tert-butyl 2-(2-oxo-3-benzylimidazolidinyl)acetate (2.51 g, 8.64 mmol) in dichloromethane (15 ml) was added trifluoroacetic acid (10 ml).

After stirring the mixture at room temperature for 1 hour, the solvent was removed under reduced pressure. The oily residue was crystallized by treating with ethyl acetate and filtered off to give 2-(2-oxo-3-benzylimidazolidinyl)acetic acid (1.56 g).

$^1$H-NMR (300 MHz, d$_6$-DMSO): δ 7.65 (1H, br s), 7.26–7.36 (5H, m), 4.41 (2H, s), 4.04 (2H, s), 3.45–3.50 (2H, m), 3.25–3.30 (2H, m).

APCIMS: 235 (MH$^+$)

mp. 132–133° C.

Reference Example 4

Preparation of Raw Compound (8) in Reaction Scheme-1

2-(2,5-dioxo-3-benzylimidazolidinyl)acetic acid (8d)

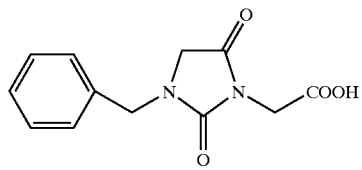

(1) To a solution of hydantoin (10.0 g, 0.10 mol) in DMF (100 ml) at 60° C. were added potassium carbonate (20.7 g, 0.15 mol) and benzyl bromoacetate (18.9 ml, 0.12 mol). After stirring the mixture at 60° C. overnight, the reaction mixture was poured into water (250 ml) and the mixture was extracted with ethyl acetate. The organic phase was washed with 5% aqueous citric acid solution and brine. The organic phase was dried over anhydrous magnesium sulfate, filtered and evaporated under reduced pressure. The crystalline residue was washed with diethyl ether, and dried to give phenylmethyl 2-(2,5-dioxoimidazolidinyl)acetate (14.9 g).

$^1$H-NMR (300 MHz, CDCl$_3$): δ 8.24 (1H, br s), 7.32–7.42 (5H, m), 5.17 (2H, s), 4.23 (2H, s), 4.03 (2H, s).

APCIMS: 249 (MH$^+$)

mp. 142–144° C.

(2) To a solution of phenylmethyl 2-(2,5-dioxoimidazolidinyl)acetate (4.0 g, 16.1 mmol) in DMF (50 ml) at 0° C. were added lithium tert-butoxide (1.6 g, 19.3 mmol) and benzyl bromide (2.1 ml, 17.7 mmol). After stirring the mixture at room temperature overnight, the reaction mixture was poured into water (100 ml) and the mixture was extracted with ethyl acetate. The organic phase was washed with water, 10% aqueous citric acid solution, saturated aqueous sodium hydrogen carbonate solution and brine. The organic solution was dried over anhydrous magnesium sulfate, filtered and evaporated under reduced pressure. The residue was purified by column chromatography (silica gel, n-hexane:ethyl acetate=3:1) to give phenylmethyl 2-(2,5-dioxo-3-benzylimidazolidinyl)acetate (3.42 g).

$^1$H-NMR (300 MHz, CDCl$_3$): δ 7.22–7.41 (10H, m), 5.20 (2H, s), 4.59 (2H, s), 4.34 (2H, s), 3.81 (2H, s).

(3) To a solution of phenylmethyl 2-(2,5-dioxo-3-benzylimidazolidinyl)acetate (3.42 g, 10.0 mmol) in THF—H$_2$O (3:1, 40 ml) was added lithium hydroxide monohydrate (0.85 g, 20.0 mmol). After stirring the mixture at 50° C. for 6 hours, the reaction mixture was alkalized with saturated aqueous sodium hydrogen carbonate solution and washed with ethyl acetate. The aqueous phase was acidified with diluted hydrochloric acid and extracted with ethyl acetate. The organic phase was washed with brine, dried over anhydrous magnesium sulfate, filtered and evaporated under reduced pressure. The residue was recrystallized with ethyl acetate and filtered off to give 2-(2,5-dioxo-3-benzylimidazolidinyl)acetic acid (1.28 g).

$^1$H-NMR (300 MHz, CDCl$_3$): δ 7.24–7.38 (10H, m), 4.57 (2H, s), 3.99 (2H, s), 3.96 (2H, d, J=5.0 Hz).

APCIMS: 249 (MH$^+$)

mp. 125–127° C.

Reference Example 5

Preparation of Raw Compound (8) in Reaction Scheme-1

2-(5-methyl-2,4-dioxo-3-benzyl-1,3-dihydropyrimidinyl)acetic acid (8e)

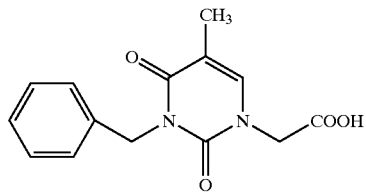

The compound 8e was obtained in the same manner as described in Reference Example 4.

$^1$H-NMR (300 MHz, CDCl$_3$): δ 8.42 (1H, br s), 7.23–7.44 (5H, m), 6.91 (1H, s), 5.13 (2H, s), 4.45 (2H, s), 1.94 (3H, s).

APCIMS: 275 (MH$^+$)

mp. 130–131° C.

Reference Example 6

Preparation of Raw Compound (4) in Reaction Scheme 1

(2S,3S)-3-amino-4-benzo[b]thiophen-3-yl-1,1,1-trifluorobutan-2-ol hydrochloride (Compound 4-1)

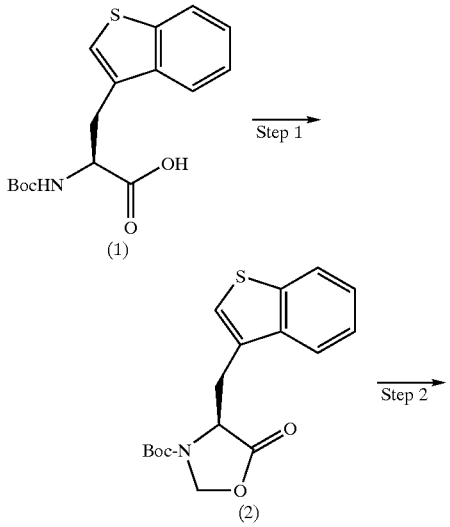

-continued

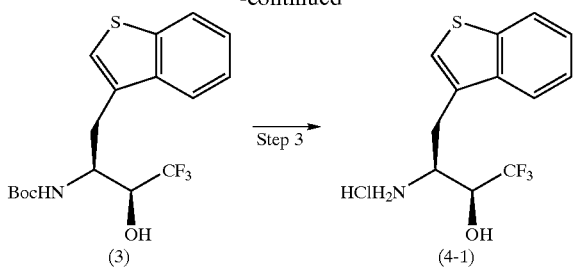

(1) To a suspension of Compound 1: (2S)-3-benzo[b]thiophen-3-yl-2-[(tert-butoxy)carbonylamino]propanoic acid (20.0 g, 62.2 mmol) in toluene (220 ml) were added paraformaldehyde (6.2 g) and p-toluene-sulfonic acid monohydrate (375 mg). After stirring the mixture at 90° C. for 3 hours, the reaction mixture was cooled in an ice bath and then washed with saturated aqueous sodium hydrogen carbonate solution and brine. The organic phase was dried over sodium sulfate, filtered and evaporated under reduced pressure. The residue was purified by column chromatography (silica gel, n-hexane:ethyl acetate 5:1) to give Compound 2: tert-butyl(4S)-4-(benzo[b]thiophen-3-yl-methyl)-5-oxo-1,3-oxazolidine-3-carboxylate (17.4 g).

$^1$H NMR (300 MHz, CDCl$_3$): δ 7.79–7.86 (2H, m), 7.32–7.37 (2H, m), 7.25 (1H, s), 5.11–5.41 (1H, m), 4.60 (1H, brs), 4.16–4.48 (1H, m), 3.37–3.74 (2H, m), 1.44 (9H, s)

LSIMS (m/z): 334 [(M+H)$^+$]

(2) To a solution of Compound 2 (25.3 g, 75.9 mmol) and trimethyl(trifluoromethyl)silane (13.5 g, 94.9 mmol) in THF (75 ml) at room temperature was added cesium fluoride (2.3 g, 15.2 mmol). The mixture was stirred for 1 hour. After adding methanol (25 ml) to the reaction mixture, the mixture was stirred at room temperature for 15 minutes. The solvent was removed under reduced pressure, and the residue was extracted with ethyl acetate and then washed with water and brine. The organic phase was dried over sodium sulfate, filtered and evaporated under reduced pressure.

The residue was dissolved in methanol (100 ml), and to the solution was added sodium borohydride (2.9 g, 75.9 mmol) at 0° C. After stirring the mixture for 1 hour, the reaction mixture was acidified with 10% aqueous citric acid solution and extracted with ethyl acetate. The organic phase was washed with 10% aqueous citric acid solution, saturated aqueous sodium hydrogen carbonate solution and brine. The organic solution was dried over sodium sulfate, filtered and evaporated under reduced pressure.

The residue was dissolved in DMF (100 ml) and water (75 ml), and to the solution was added potassium carbonate (12.6 g, 91.1 mmol) at room temperature. After stirring the mixture for 1 hour, the reaction mixture was acidified with 10% aqueous citric acid solution and extracted with ethyl acetate. The organic phase was washed with 10% aqueous citric acid solution, saturated aqueous sodium hydrogen carbonate solution and brine. The organic solution was dried over sodium sulfate, filtered and evaporated under reduced pressure. The residue was purified by column chromatography (silica gel, n-hexane:ethyl acetate 10:1) to give Compound 3: N-[(1S,2S)-1-(benzo[b]thiophen-3-yl-methyl)-3,3,3-trifluoro-2-hydroxypropyl](tert-butoxy)carboxamide (22.4 g).

$^1$H NMR (300 MHz, CDCl$_3$): δ 7.80–7.89 (2H, m), 7.35–7.44 (2H, m), 7.25 (1H, s), 5.05 (1H, brs), 4.81–4.83 (1H, d, J=7.5 Hz), 3.99–4.02 (2H, m), 3.23–3.40 (2H, m), 1.44 (9H, s)

LSIMS (m/z): 376 [(M+H)$^+$]
m.p.: 118–120° C.

(3) To Compound 3 (3.75 g, 10 mmol) was added 4 mol/1000 ml-hydrogen chloride in 1,4-dioxane solution (25 ml). After stirring the mixture at room temperature for 30 minutes, the solvent was removed under reduced pressure. The residue was crystallized by treating with diethyl ether and filtered off to give Compound 4-1: (2S,3S)-3-amino-4-benzo[b]thiophen-3-yl-1,1,1-trifuluorobutan-2-ol hydrochloride (3.1 g).

$^1$H NMR (300 MHz, CDCl$_3$): δ 8.02–8.05 (1H, m), 7.91–7.94 (1H, m), 7.71 (1H, brs), 7.40–7.50 (2H, m), 4.12–4.15 (1H, m), 3.70 (1H, brs), 3.28–3.32 (2H, m)

APCIMS: 276 (MH$^+$)
m.p.: 123–125° C.

Reference Example 7

Preparation of Raw Compound (4) in Reaction Scheme-1

(2S,3S)-3-amino-1,1,1-trifuluoro-4-(2-naphthyl)butan-2-ol (Compound 4-2)

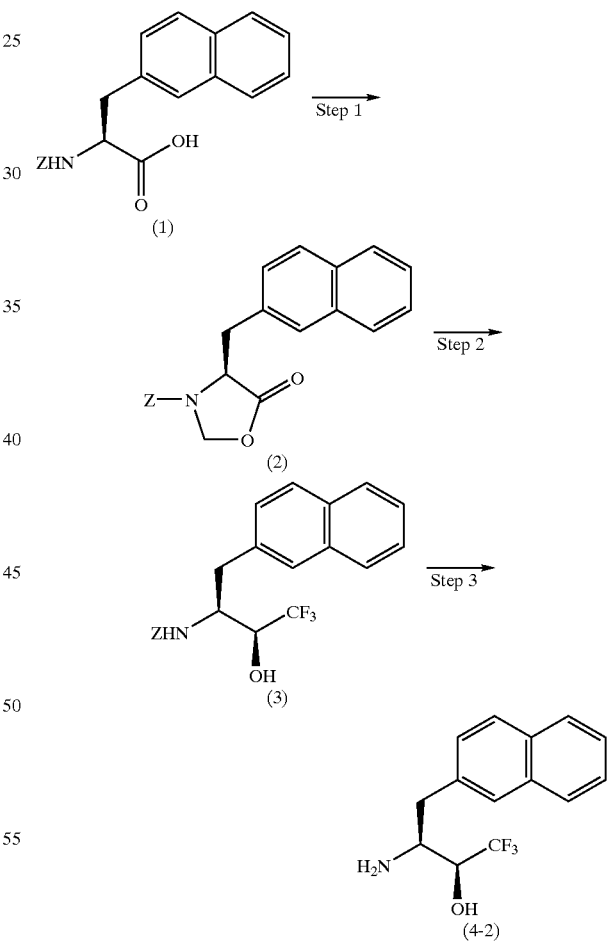

(1) To a suspension of Compound 1: (2S)-3-(2-naphthyl)-2-[(phenylmethoxy)carbonylamino]propanoic acid (14.3 g, 40.9 mmol) in toluene (140 ml) were added paraformaldehyde (2.0 g) and p-toluenesulfonic acid monohydrate (600 mg). After refluxing the mixture for 30 minutes, the reaction mixture was cooled in an ice bath and then washed with saturated aqueous sodium hydrogen carbonate solution and brine. The organic phase was dried over sodium sulfate, filtered and evaporated under reduced pressure. The residue was crystallized by treating with isopropyl ether to give Compound 2: phenylmethyl (4S)-4-(2-naphthylmethyl)-5-oxo-1,3-oxazolidine-3-carboxylate (11.8 g).

$^1$H NMR (300 MHz, CDCl$_3$): δ 7.68–7.81 (3H, m), 7.40–7.60 (8H, m), 7.18 (1H, brs), 5.21–5.29 (3H, m), 4.64 (1H, s), 4.23 (1H, s), 3.36 (1H, s)

APCIMS: 362 (MH$^+$)

m.p.: 88–89° C.

(2) To a solution of Compound 2 (11.8 g, 32.7 mmol) and trimethyl(trifluoromethyl)silane (5.8 g, 40.8 mmol) in THF (30 ml) with cooling in an ice bath was added cesium fluoride (1.0 g, 6.53 mmol). The mixture was stirred at room temperature for 30 minutes, and the solvent was removed under reduced pressure. After adding methanol (60 ml) to the residue, the mixture was stirred at room temperature for 15 minutes.

The solution was cooled at 0° C. in an ice bath and sodium borohydride (1.2 g, 32.7 mmol) was added thereto. After stirring the mixture for 30 minutes, to the solution were added water (45 ml) and potassium carbonate (5.4 g, 39.2 mmol). After the solution was stirred at room temperature for 30 minutes, methanol was removed under reduced pressure and the residue was extracted with ethyl acetate. The organic phase was washed with 10% aqueous citric acid solution, saturated aqueous sodium hydrogen carbonate solution and brine. The organic solution was dried over sodium sulfate, filtered and evaporated under reduced pressure. The residue was purified by column chromatography (silica gel, n-hexane:ethyl acetate 9:1) to give Compound 3: N-[(1S,2S)-3,3,3-trifluoro-2-hydroxy-1-(2-naphthylmethyl) propyl](phenylmethoxy)carboxamide (8.4 g).

$^1$H NMR (300 MHz, CDCl$_3$): δ 7.74–7.84 (3H, m), 7.65 (1H, brs), 7.46–7.51 (2H, m), 7.33 (6H, m), 5.22–5.25 (1H, m), 5.12 (2H, s), 4.10–4.12 (2H, m), 3.98 (1H, m), 3.28 (1H, m) 3.17–3.19 (1H, m)

APCIMS: 404 (MH$^+$)

m.p.: 172–174° C.

(3) To a solution of Compound 3 (8.4 g, 20.8 mmol) in ethyl acetate 100 ml was added 20 wt. % palladium hydroxide (1.5 g). After stirring the mixture at room temperature under a hydrogen atmosphere for 3 hours, the catalyst was removed by filtration. The filtrate was evaporated under reduced pressure and the residue as white solid was washed with n-hexane to give Compound 4-2: (2S,3S)-3-amino-1,1,1-trifluoro-4-(2naphthyl)butan-2-ol (5.3 g).

$^1$H NMR (300 MHz, CDCl$_3$): δ 7.79–7.85 (3H, m), 7.66(1H, s), 7.45–7.53 (2H, m), 7.33–7.36 (1H, m), 3.71–3.78 (1H, m), 3.62–3.68 (1H, m), 3.02–3.09 (1H, m), 2.78–2.90 (1H, m)

APCIMS: 270 (MH$^+$)

p.: 122–125° C.

Reference Example 8

Preparation of Raw Compound (4) in Reaction Scheme-1

The compounds as shown in Table 1 were obtained in the same manner as described in Reference Example 6 or 7.

TABLE 1 structure: H$_2$N-CH(CH$_2$)$_n$-R$^1$ / CH(OH)-CF$_3$

| Comp. No. | R$^1$ | n | MH$^+$* | m.p.° C. |
|---|---|---|---|---|
| 4-3 | Ph | 1 | 220 | 106–110 |
| 4-4 | Ph | 2 | 234 | 105–107 |
| 4-5 | 2-Cl—Ph | 1 | 254 | 114–117 |
| 4-6 | 2-F—Ph | 1 | 238 | sublimation |
| 4-7 | 3-Cl—Ph | 1 | 254 | — |
| 4-8 | 4-Cl—Ph | 1 | 254 | 158–159 |
| 4-9** | 4-F—Ph | 1 | 238 | 203–205 |
| 4-10 | 2,3,4,5,6-F—Ph | 1 | 310 | sublimation |
| 4-11** | 4-I—Ph | 1 | 346 | 144–145 |
| 4-12** | 3-Me—Ph | 1 | 234 | 82–84 |
| 4-13 | 4-Me—Ph | 1 | 234 | 124–125 |
| 4-14** | 4-Et—Ph | 1 | 248 | 109–110 |
| 4-15 | 4-OH—Ph | 1 | — | — |
| 4-16 | 4-MeO—Ph | 1 | 250 | 106–108 |
| 4-17** | 2-CF$_3$—Ph | 1 | 288 | 78–81 |
| 4-18** | 4-CF$_3$—Ph | 1 | 288 | 134–136 |
| 4-19 | 3-methylbenzothiophene-S,S-dioxide | 1 | — | — |
| 4-20** | 2-methylthiophene | 1 | — | — |
| 4-21 | cyclohexyl | 1 | 212 | 90–91 |
| 4-22** | 3-methylbenzofuran | 1 | — | — |
| 4-23 | 3-methylindole | 1 | 259 | 136–139 |
| 4-24** | 1-methylnaphthyl | 1 | 270 | 101–103 |
| 4-25** | methylindane | 1 | 260 | 87–89 |
| 4-26** | methyltetrahydronaphthyl | 1 | 275 | 86–89 |
| 4-27 | cyclopropyl | 1 | 184 LSIMS | — |

TABLE 1-continued (CH₂)n-R¹ structure with H₂N, CF₃, OH

| Comp. No. | R¹ | n | MH+* | m.p.° C. |
|---|---|---|---|---|
| 4-28** | 2-methylbenzo[b]thiophene | 1 | 276 | — |

*APCIMS
**diastereomer mixture

Example 1

Preparation of N-[(1S)-2-((2S)-2-{N-[(1S)-1-(benzo[b]thiophen-3-yl-methyl)-3,3,3-trifluoro-2-oxopropyl]carbamoyl}pyrrolidinyl)-1-(methylethyl)-2-oxoethyl](3,5-dimethylisoxazol-4-yl)carboxamide (Compound I-A-1)

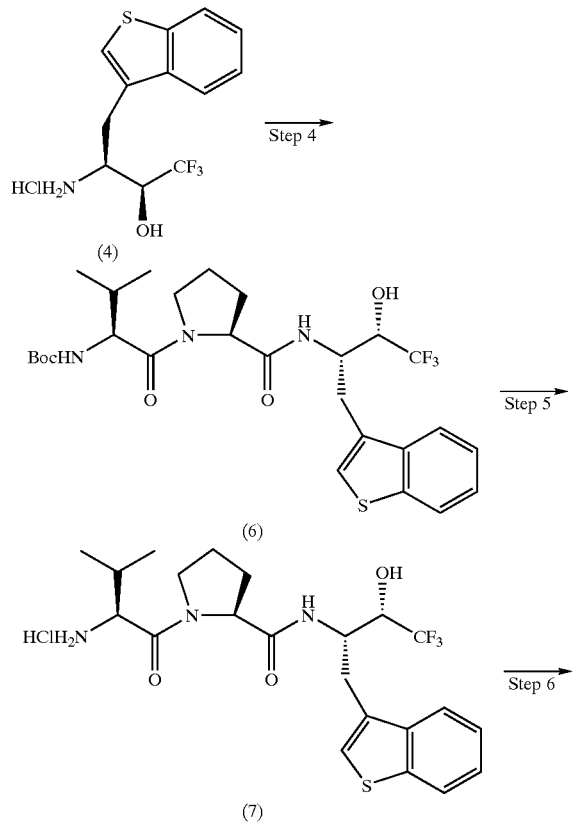

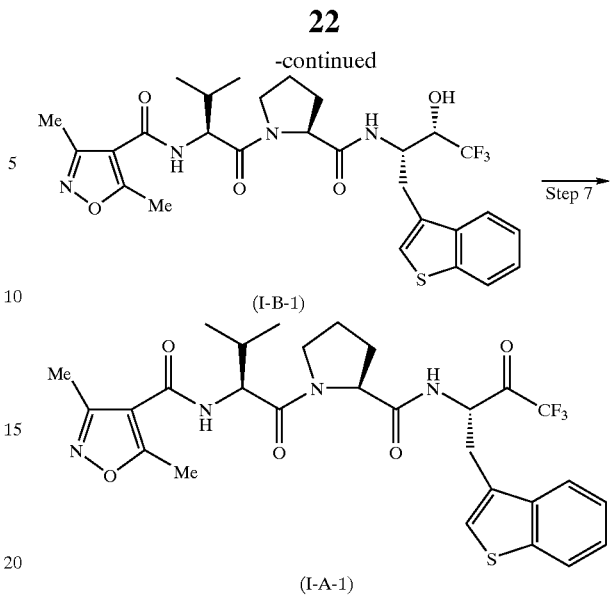

(1) (Step 4) To a solution of Compound 4: (2S,3S)-3-amino-4-benzo[b]thiophen-3-yl-1,1,1-trifuluorobutan-2-ol hydrochloride (14.1 g, 45.2 mmol) in pyridine (135 ml) were added N-(tert-butoxycarbonyl)-L-valyl-L-proline (Compound 5 in reaction Scheme-1) (14.2 g, 45.2 mmol) and 1-ethyl-3-(3-dimethylaminopropyl)carbodiimide hydrochloride (9.1 g, 47.5 mmol). The reaction mixture was stirred at room temperature for 15 hours and then the solvent was removed under reduced pressure. The residue was extracted with ethyl acetate and then washed with 5% aqueous potassium hydrogen sulfate solution, water and brine. The organic solution was dried over sodium sulfate, filtered and evaporated under reduced pressure. The residue was purified by column chromatography (silica gel, n-hexane:ethyl acetate 2:1) to give Compound 6: N-[(1S)-2-((2S)-2-{N-[(1S,2S)-1-(benzo[b]thiophen-3-yl-methyl)-3,3,3-trifluoro-2-hydroxypropyl]carbamoyl}pyrrolidinyl-1-(methylethyl)-2-oxoethyl](tert-butoxy)carboxamide (19.8 g).

APCIMS: 572 (MH⁺)

(2) (Step 5) To Compound 6 (19.8 g, 34.6 mmol) was added 4 mol/1000 ml hydrogen chloride in 1,4-dioxane solution (90 ml). After stirring at room temperature for 30 minutes, the solvent was removed under reduced pressure. The residue as white powder was washed with n-hexane to give Compound 7: [(2S)-1-((2S)-2-amino-3-methylbutanoyl)pyrrolidin-2-yl]-N-[(1S,2S)-1-(benzo[b]thiophen-3-yl-methyl)-3,3,3-trifluoro-2-hydroxypropyl]carboxamide hydrochloride (17.6 g).

APCIMS: 472 (MH⁺)

(3) (Step 6) To a solution of Compound 7 (10.2 g, 20.1 mmol) in pyridine (100 ml) were added 3,5-dimethylisoxazole-4-carboxylic acid (Compound 8 in Reaction Scheme-1) (2.8 g, 20.1 mmol) and 1-ethyl-3-(3-dimethylaminopropyl)carbodiimide (4.0 g, 21.1 mmol). The reaction mixture was stirred at room temperature for 15 hours and then the solvent was removed under reduced pressure. The residue was extracted with ethyl acetate and then washed with 5% aqueous potassium hydrogen sulfate solution, water and brine. The organic solution was dried over sodium sulfate, filtered and evaporated under reduced pressure. The residue was subjected to column chromatography on CHP20P (Mitsubishi Chemical Co. Ltd.), and eluted with a gradient of 30 to 70% acetonitrile in water under a medium pressure to give Compound I-B-1: N-[(1S)-

2-((2S)-2-{N-[(1S,2S)-1-(benzo[b]thiophen-3-yl-methyl)-3,3,3-trifluoro-2-hydroxypropyl]carbamoyl}pyrrolidinyl)-1-(methylethyl)-2-oxoethyl](3,5-dimethylisoxazol-4-yl)carboxamide (8.2 g).

APCIMS: 595 (MH$^+$)

(4) (Step 7) To a solution of Compound I-B-1 (8.2 g, 13.8 mmol) in dichloromethane (160 ml) were added tert-butyl alcohol (1.4 ml, 13.8 mmol) and Dess-Martin periodinane (11.7 g, 27.6 mmol). The reaction mixture was stirred at room temperature for 15 hours and then the solvent was removed under reduced pressure. The residue was extracted with ethyl acetate and then washed with saturated aqueous sodium thiosulfate solution, saturated aqueous sodium hydrogen carbonate solution and brine. The organic solution was dried over sodium sulfate, filtered and evaporated under reduced pressure. The residue was subjected to column chromatography on CHP20P, and eluted with a gradient of 30 to 70% acetonitrile in water under a medium pressure to give Compound I-A-1: N-[(1S)-2-((2S)-2-{N-[(1S)-1-(benzo[b]thiophen-3-yl-methyl)-3,3,3-trifluoro-2-oxopropyl]carbamoyl}pyrrolidinyl)-1-(methylethyl)-2-oxoethyl](3,5-dimethylisoxazol-4-yl)carboxamide (5.9 g).

APCIMS: 572 (MH$^+$)

$^1$H NMR (300 MHz, d$_6$-DMSO): δ 0.93 (3H, d), 0.95 (3H, d) 1.69–2.13 (4H, m), 2.25 (3H, s), 2.47 (3H, s), 2.89 (1H, dd), 3.28–3.45 (3H, m), 3.52–3.59 (1H, m), 3.73–3.80 (1H, m), 4.37–4.46 (2H, m), 7.26–7.48 (4H, m), 7.78 (1H, d), 7.93–8.11 (2H, m).

Elemental Analysis for C$_{28}$H$_{31}$F$_3$N$_4$O$_5$S.0.25 H$_2$O:

Calcd.: C, 56.32; H, 5.32; F, 9.54; N, 9.38; S, 5.37

Found: C, 56.04; H, 5.51; F, 9.34; N, 9.11; S, 5.13

Example 2

Preparation of N-[(1S)-2-((2S)-2-{N-[(1S)-3,3,3-trifluoro-1-(2-naphthylmethyl)-2-oxopropyl]carbamoyl}pyrrolidinyl)-1-(methylethyl)-2-oxoethyl]-(3,5-dimethylisoxazol-4-yl)carboxamide (Compound I-A-2)

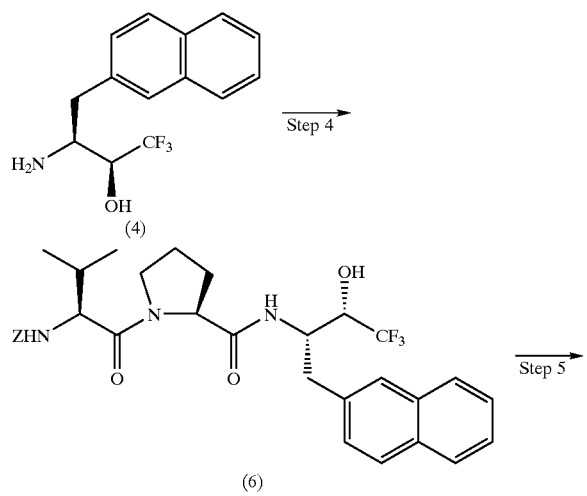

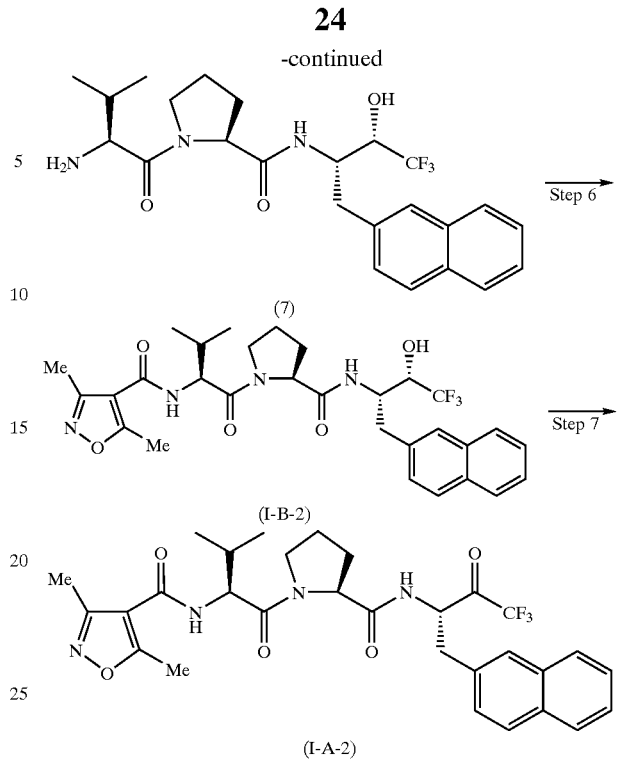

(1) (Step 4) To a solution of Compound 4: (2S,3S)-3-amino-1,1,1-trifuluoro-4-(2-naphthyl)butan-2-ol (0.93 g, 3.44 mmol) in dichloromethane 15 ml were added N-(benzyloxycarbonyl)-L-valyl-L-proline (Compound 5 in Reaction Scheme-1) (1.20 g, 3.44 mmol) and 1-ethyl-3-(3-dimethylaminopropyl)carbodiimide hydrochloride (0.69 g, 3.62 mmol). The reaction mixture was stirred at room temperature for 15 hours and then the solvent was removed under reduced pressure. The residue was extracted with ethyl acetate and then washed with 10% hydrochloric acid, saturated aqueous sodium hydrogen carbonate solution and brine. The organic solution was dried over sodium sulfate, filtered and evaporated under reduced pressure. The residue was subjected to column chromatography on CHP20P, and eluted with a gradient of 20 to 70% acetonitrile in water under a medium pressure to give Compound 6: N-[(1S)-2-((2S)-2-{N-[(1S,2S)-3,3,3-trifluoro-2-hydroxy-1-(2-naphthylmethyl)propyl]carbamoyl}pyrrolidinyl)-1-(methylethyl)-2-oxoethyl](phenylmethoxy)carboxamide (1.6 g).

APCIMS: 600 (MH$^+$)

(2) (Step 5) To a solution of Compound 6 (1.6 g, 2.67 mmol) in ethyl acetate (20 ml) was added 20 wt. % palladium hydroxide (0.3 g). After stirring at room temperature under a hydrogen atmosphere for 3 hours, the catalyst was removed by filtration. The filtrate was evaporated under reduced pressure to give Compound 7: [(2S)-1-((2S)-2-amino-3-methylbutanoyl)pyrrolidin-2-yl]-N-[(1S,2S)-3,3,3-trifluoro--2-hydroxy-1-(2-naphthylmethyl)propyl]carboxamide (1.24 g).

APCIMS: 466 (MH$^+$)

(3) (Step 6) To a solution of Compound 7 (1.24 g, 2.67 mmol) in dichloromethane (20 ml) were added 3,5-dimethylisoxazole-4-carboxylic acid (Compound 8 in Reaction Scheme 1) (0.38 g, 2.67 mmol) and 1-ethyl-3 3-(3-dimethylamino propyl)carbodiimide hydrochloride (0.54 g, 2.80 mmol). The reaction mixture was stirred at room temperature for 15 hours and then the solvent was removed under reduced pressure. The residue was extracted with ethyl acetate and then washed with 10% hydrochloric acid, saturated aqueous sodium hydrogen carbonate solution and brine. The organic solution was dried over sodium sulfate, filtered and evaporated under reduced pressure. The residue was subjected to column chromatography on CHP20P, and eluted with a gradient of 20 to 70% acetonitrile in water under a medium pressure to give Compound I-B-2: N-[(1S)-2-((2S)-2-{N-[(1S,2S)-3,3,3-trifluoro-2-hydroxy-1-(2-naphthylmethyl)propyl]carbamoyl}pyrrolidinyl)-1-methylethyl)-2-oxoethyl](3,5-dimethylisoxazol-4-yl)carboxamide (1.2 g).

APCIMS: 589 (MH$^+$)

(4) (Step 7) To a solution of Compound I-B-2 (1.2 g, 2.04 mmol) in dichloromethane (25 ml) were added tert-butyl alcohol (0.20 ml, 2.04 mmol) and Dess-Martin periodinane (1.7 g, 4.08 mmol). The reaction mixture was stirred at room temperature for 15 hours and then the solvent was removed under reduced pressure. The residue was extracted with ethyl acetate and then washed with saturated aqueous sodium thiosulfate solution, saturated aqueous sodium hydrogen carbonate solution and brine. The organic solution was dried over sodium sulfate, filtered and evaporated under reduced pressure. The residue was subjected to column chromatography on CHP20P, and eluted with a gradient of 20 to 70% acetonitrile in water under a medium pressure to give Compound I-A-2: N-[(1S)-2-((2S)-2-{N-[(1S)-3,3,3-trifluoro-1-(2-naphthylmethyl)-2-oxopropyl]carbamoyl}pyrrolidinyl)-1-(methylethyl)-2-oxoethyl](3,5-dimethylisoxazol-4-yl)carboxamide (0.60 g).

APCIMS: 587 (MH$^+$)

$^1$H NMR (300 MHz, d$_6$-DMSO): δ 8.05 (1H, d), 7.71–7.94 (4H, m), 7.40–7.45 (2H, m), 7.16–7.22 (2H, m), 4.28–4.42 (3H, m), 3.70 (1H, m), 3.50 (1H, m), 3.30–3.34 (3H, m), 2.88 (1H, dd), 2.40 (3H, s), 2.30 (3H, s), 1.99–2.07 (1H, m), 1.58–1.91 (2H, m), 0.87 (3H, d), 0.85 (3H, d)

Elemental Analysis for C$_{30}$H$_{33}$F$_3$N$_4$O$_5$·0.75 H$_2$O
Calcd.: C, 60.04; H, 5.79; F, 9.50; N, 9.34
Found: C, 60.06; H, 5.85; F, 9.53; N, 9.16

Example 3

Preparation of Compounds I-A

The following compounds disclosed in Tables 2 to 12 were obtained in the same manner as described in Example 1 or 2. In these tables, the mass spectrometry is APCIMS unless specified otherwise.

TABLE 2

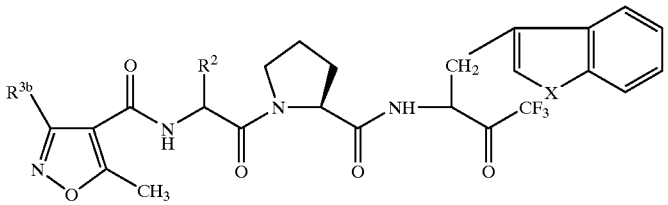

| Comp. No. | R$^{3b}$ | R$^2$ | X | MH$^+$ | Elemental Analyses Calcd.(Found) |
|---|---|---|---|---|---|
| I-A-3 | Me | Me (ethyl-like) | S | 579 | C$_{27}$H$_{29}$F$_3$N$_4$O$_5$S·1.20 H$_2$O·0.05 AcOEt: C 54.03(54.20), H 5.30 (5.42), F 9.43(9.21), N 9.27 (8.98), S 5.30(5.05) |
| I-A-4 | Me | Me-CH-CH$_2$-Me | S | 607 | C$_{29}$H$_{33}$F$_3$N$_4$O$_5$S·0.75 H$_2$O: C 56.16(56.35), H 5.61(5.62), F 9.19(9.07), N 9.03(9.05), S 5.17(4.90) |
| I-A-5 | Me | Me | S | 565 | C$_{26}$H$_{27}$F$_3$N$_4$O$_5$S·0.75 H$_2$O: C 54.02(54.12), H 4.97(5.04), F 9.86(9.65), N 9.69(9.48), S 5.55(5.28) |
| I-A-6 | Me | cyclohexyl | S | 633 | C$_{31}$H$_{35}$F$_3$N$_4$O$_5$S·1.00 H$_2$O: C 57.22(57.26), H 5.73(5.88), F 8.76(8.57), N 8.61(8.41), S 4.93(4.67) |
| I-A-7 | Ph | Me-C-Me | S | 655 | C$_{33}$H$_{33}$F$_3$N$_4$O$_5$S·0.75 H$_2$O: C 59.32(59.19), H 5.20(5.28), F 8.53(8.42), N 8.38(8.59), S 4.80(4.63) |
| I-A-8 | Me | benzyl | S | 641 | C$_{32}$H$_{31}$F$_3$N$_4$O$_5$S·0.25 H$_2$O·0.25 AcOEt: C 59.41(59.09), H 5.06 (5.28), F 8.54(8.54), N 8.40(8.01), S 4.81(4.52) |

TABLE 2-continued

[Structure: R3b-substituted isoxazole-carboxamide-R2-prolyl-NH-CH(CH2-indole/benzofuran X)-C(O)-CF3]

| Comp. No. | R3b | R2 | X | MH+ | Elemental Analyses Calcd.(Found) |
|---|---|---|---|---|---|
| I-A-9 | Me | Me-iPr-Me | O | 577 | C28H31F3N4O6·1.25 H2O: C 56.14 (56.26), H 5.64(5.70), F 9.51 (9.26), N 9.35(9.11) |
| I-A-10 | Me | Me-iPr-Me | NH | 576 | C28H32F3N5O5·0.50 H2O·0.15 AcOEt: C 57.46(57.48), H 5.77 (5.83), F 9.53(9.40), N 11.72 (11.50) |
| I-A-11 | Me | Me-iPr-Me | SO2 | 625 | C28H31F3N4O7S·0.75 H2O·0.25 AcOEt: C 52.76(52.52), H 5.27 (5.44), F 8.63(8.36), N 8.49(8.34), S 4.86(4.66) |
| I-A-12 | Me | H | S | 551 | C25H25F3N4O5S·1.00 H2O·0.15 AcOEt: C 52.85(52.80), H 4.89 (4.95), F 9.80(9.74), N 9.63(9.34), S 5.51(5.27) |

TABLE 3

[Structure: 3,5-dimethylisoxazole-4-carboxamide-R2-prolyl-NH-CH(CH2-R1)-C(O)-CF3]

| Comp. No. | R2 | R1 | MH+ | Elemental Analyses Calcd.(Found) |
|---|---|---|---|---|
| I-A-13 | Et (Me-CH) | 2-naphthyl | 573 | C29H31F3N4O5·1.05 H2O·0.10 AcOEt: C 58.82(58.89), H 5.69 (5.76), F 9.49(9.20), N 9.33(9.27) |
| I-A-14 | benzyl (PhCH2-CH) | 2-pyridyl | 585 | C30H31F3N4O5·1.00 H2O: C 59.80 (59.72), H 5.52(5.49), F 9.46 (9.28), N 9.30(9.26) |
| I-A-15 | Me-iPr-Me | 1-naphthyl | 587 | C30H33F3N4O5·1.75H2O: C 58.29 (58.38), H 5.95(5.88), F 9.22 (9.13), N 9.06(8.73) |
| I-A-16 | Me-iPr-Me | cyclohexyl | 543 | C26H37F3N4O5·1.25H2O: C 55.26 (55.22), H 7.05(6.94), F 10.09 (10.10), N 9.91(9.81) |
| I-A-17 | Me-iPr-Me | 2-thienyl | 543 | C24H29F3N4O5S·1.00H2O: C 51.42 (51.18), H 5.57(5.65), F 10.17 (10.03), N 9.99(9.80), S 5.72 (5.51) |

TABLE 3-continued

| Comp. No. | R² | R¹ | MH⁺ | Elemental Analyses Calcd.(Found) |
|---|---|---|---|---|
| I-A-18 | Me⤒Me (isopropyl) | indanyl | 577 | $C_{29}H_{35}F_3N_4O_5 \cdot 0.50H_2O$: C 59.48 (59.41), H 6.20(6.09), F 9.73 (9.58), N 9.57(9.50) |
| I-A-19 | Me⤒Me (isopropyl) | tetrahydronaphthyl | 591 | $C_{30}H_{37}F_3N_4O_5 \cdot 1.25H_2O$: C 58.77 (58.77), H 6.49(6.43), F 9.30 (9.15), N 9.14(9.12) |

TABLE 4

| Comp. No. | R² | R¹ | MH⁺ | Elemental Analyses Calcd.(Found) |
|---|---|---|---|---|
| I-A-20 | Me⤒Me (isopropyl) | benzothienyl | 596 | $C_{26}H_{28}F_3N_5O_4S_2 \cdot 0.90\ H_2O \cdot 0.10$ AcOEt: C 51.09(51.11), H 4.97 (5.12), F 9.18(8.89), N 11.28 (11.13), S 10.33(10.10) |
| I-A-21 | Et (Me on CH) | benzothienyl | 582 | $C_{25}H_{26}F_3N_5O_4S_2 \cdot 0.90\ H_2O \cdot 0.10$ AcOEt: C 50.29(50.51), H 4.75 (4.72), F 9.39(9.19), N 11.54 (11.52), S 10.57(10.27) |
| I-A-22 | Me⤒Me (isopropyl) | naphthyl | 590 | $C_{28}H_{30}F_3N_5O_4S \cdot 0.90\ H_2O \cdot 0.05$ AcOEt: C 55.50(55.71), H 5.32 (5.31), F 9.34(9.09), N 11.48 (11.18), S 5.25(5.01) |
| I-A-23 | Et | naphthyl | 576 | $C_{27}H_{28}F_3N_5O_4S \cdot 1.00\ H_2O$: C 54.63 (54.76), H 5.09(5.16), F 9.60 (9.43), N 11.80(11.52), S 5.40 (5.22) |
| I-A-24 | Me⤒Me (isopropyl) | indanyl | 580 | $C_{27}H_{32}F_3N_5O_4S \cdot 1.00\ H_2O$: C 54.26 (54.02), H 5.73(5.77), F 9.54 (9.47), N 11.72(11.58), S 5.37 (5.24) |
| I-A-25 | Me⤒Me (isopropyl) | tetrahydronaphthyl | 594 | $C_{28}H_{34}F_3N_5O_4S \cdot 0.75\ H_2O$: C 55.39 (55.35), H 5.89(5.90), F 9.39 (9.23), N 11.53(11.44), S 5.28 (5.19) |

TABLE 5

| Comp. No. | $R^{3a}$ | $R^{3b}$ | $R^{1a}$ | MH$^+$ | Elemental Analyses Calcd.(Found) |
|---|---|---|---|---|---|
| I-A-26 | Me | Me | H | 537 | $C_{26}H_{31}F_3N_4O_5 \cdot 0.50\ H_2O$: C 57.24 (57.40), H 5.91(5.77), F 10.45 (10.30), N 10.27(10.21) |
| I-A-27 | Me | Me | 2-F | 555 | $C_{26}H_{30}F_4N_4O_5 \cdot 1.25\ H_2O$: C 54.12 (54.20), H 5.68(5.56), F 13.17 (12.97), N 9.71(9.62) |
| I-A-28 | Me | Me | 4-OH | 553 | $C_{26}H_{31}F_3N_4O_6 \cdot 0.85\ H_2O \cdot 0.05\ AcOEt$: C 54.99(55.07), H 5.83(5.87), F 9.88(9.92), N 9.79(9.50) |
| I-A-29 | Me | Me | 4-Cl | 571 | $C_{26}H_{30}ClF_3N_4O_5 \cdot 1.00\ H_2O$: C 53.02 (53.18), H 5.48(5.57), Cl 6.02(5.89), F 9.68(9.46), N 9.51(9.26) |
| I-A-30 | Me | Me | 4-F | 555 | $C_{26}H_{30}F_4N_4O_5 \cdot 1.75\ H_2O$: C 53.28 (53.39), H 5.76(5.68), F 12.97 (12.93), N 9.56(9.30) |
| I-A-31 | Me | H$_2$N—CO | H | 566 | $C_{26}H_{30}F_3N_5O_6 \cdot 0.50\ H_2O$: C 54.35 (54.52), H 5.44(5.45), F 9.92(9.77), N 12.19(11.91) |
| I-A-32 | Me | Ph | H | 599 | $C_{31}H_{33}F_3N_4O_5 \cdot 1.25\ H_2O$: C 59.94 (59.78), H 5.76(5.55), F 9.18(9.13), N 9.02(8.82) |
| I-A-33 | Me | Me | 2-Me | 551 | $C_{27}H_{33}F_3N_4O_5 \cdot 1.00\ H_2O$: C 57.03 (56.85), H 6.20(6.03), F 10.02 (10.01), N 9.85(9.45) |
| I-A-34 | Ac | Me | H | 565 | $C_{27}H_{31}F_3N_4O_6$: C 57.44(57.64), H 5.53(5.83), F 10.10(9.83), N 9.92 (9.82) |
| I-A-35 | Me | Me | 4-Me | 551 | $C_{27}H_{33}F_3N_4O_5 \cdot 1.00\ H_2O$: C 57.03 (56.85), H 6.20(6.01), F 10.02 (10.06), N 9.85(9.74) |
| I-A-36 | Me | 2,6-F,Cl—Ph | H | 651 | $C_{31}H_{31}ClF_4N_4O_5 \cdot 1.50\ H_2O$: C 54.91 (55.14), H 5.05(4.98), Cl 5.23 (5.23), F 11.21(10.95), N 8.26 (7.96) |
| I-A-37 | Me | Me | 4-MeO | 567 | $C_{27}H_{33}F_3N_4O_6 \cdot 0.50\ H_2O$: C 56.34 (56.28), H 5.95(5.89), F 9.90 (9.92), N 9.73(9.62) |
| I-A-38 | Me | Me | 3-Cl | 571 | $C_{26}H_{30}ClF_3N_4O_5 \cdot 1.50\ H_2O$: C 52.22 (52.45), H 5.56(5.35), Cl 5.93 (5.82), F 9.53(9.48), N 9.37(9.09) |
| I-A-39 | Me | Me | 2-Cl | 571 | $C_{26}H_{30}ClF_3N_4O_5 \cdot 1.30\ H_2O \cdot 0.10\ AcOEt$: C 52.57(52.43), H 5.58 (5.31), Cl 5.88(5.80), F 9.45(9.48), N 9.29(8.89) |
| I-A-40 | Me | Me | 3-Me | 551 | $C_{27}H_{33}F_3N_4O_5 \cdot 0.75\ H_2O$: C 57.49 (57.21), H 6.16(6.14), F 10.10 (10.23), N 9.93(9.78) |
| I-A-41 | Me | 2-Cl—Ph | H | 633 | $C_{31}H_{32}ClF_3N_4O_5 \cdot 0.75\ H_2O$: C 57.59(57.72), H 5.22(5.34), Cl 5.48(5.39), F 8.81(8.70), N 8.67(8.39) |
| I-A-42 | Me | Me | 4-I | 663 | $C_{26}H_{30}F_3IN_4O_5 \cdot 1.50\ H_2O \cdot 0.10\ AcOEt$: C 45.41(45.54), H 4.88(4.90), F 8.16(8.12), I 18.17(17.87), N 8.02(7.81) |
| I-A-43 | Me | Me | 4-Cl | 571 | $C_{26}H_{30}ClF_3N_4O_5 \cdot 1.50\ H_2O$: C 52.22(52.27), H 5.56(5.45), Cl 5.93(5.84), F 9.53(9.64), N 9.37(9.27) |
| I-A-44 | Me | Et | H | 551 | $C_{27}H_{33}F_3N_4O_5 \cdot 1.50\ H_2O$: C 56.15(56.11), H 6.28(6.05), F 9.87(9.88), N 9.70(9.46) |

TABLE 5-continued

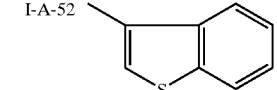

| Comp. No. | R³ᵃ | R³ᵇ | R¹ᵃ | MH⁺ | Elemental Analyses Calcd.(Found) |
|---|---|---|---|---|---|
| I-A-45 | Me | 2,6-F,Cl—Ph | H | 667 | $C_{31}H_{31}Cl_2F_3N_4O_5 \cdot 1.25\ H_2O$: C 53.96(53.83), H 4.89(4.97), Cl 10.28(10.11), F 8.26 (8.33), N 8.12(8.00) |
| I-A-46 | Me | Me | 2-CF₃ | 605 | $C_{27}H_{30}F_6N_4O_5 \cdot 0.75\ H_2O$: C 52.47(52.28), H 5.14(5.24), F 18.44(18.50), N 9.06(8.79) |
| I-A-47 | 4-CF₃—Ph | Me | H | 667 | $C_{32}H_{32}F_6N_4O_5 \cdot 0.75\ H_2O$: C 56.51(56.42), H 4.96(4.94), F 16.76(16.63), N 8.24(8.11) |

TABLE 6

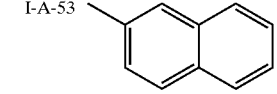

| Comp. No. | R³ᵃ | R³ᵇ | R¹ᵃ | n | MH⁺ | Elemental Analyses Calcd.(Found) |
|---|---|---|---|---|---|---|
| I-A-48 | Me | Me | 4-Et | 1 | 565 | $C_{28}H_{35}F_3N_4O_5 \cdot 0.50\ H_2O$: C 58.63(58.67), H 6.33(6.22), F 9.94(9.80), N 9.77(9.66) |
| I-A-49 | Me | Me | H | 2 | 551 | $C_{27}H_{33}F_3N_4O_5 \cdot 0.25\ H_2O$: C 58.42(58.31), H 6.08(6.02), F 10.27(10.32), N 10.09(10.00) |
| I-A-50 | Me | Me | 2,3,4,5,6-F | 1 | 627 | $C_{26}H_{26}F_8N_4O_5 \cdot 1.10\ H_2O \cdot 0.20$ AcOEt: C 48.48 (48.27), H 4.52(4.56), F 22.89(22.75), N 8.44(8.48) |
| I-A-51 | Me | Me | 4-CF₃ | 1 | 605 | $C_{27}H_{30}F_6N_4O_5 \cdot 1.50\ H_2O$: C 51.35(51.40), H 5.27(5.22), |

TABLE 6-continued

| Comp. No. | R³ᵃ | R³ᵇ | R¹ᵃ | n | MH⁺ | Elemental Analyses Calcd.(Found) |
|---|---|---|---|---|---|---|
| | | | | | | F 18.05(18.20), N 8.87 (8.67) |

TABLE 7

| Comp. No. | R¹ | MH⁺ | Elemental Analyses Calcd.(Found) |
|---|---|---|---|
| I-A-52 | ![thiophene] | 632 LSIMS | $C_{29}H_{28}F_3N_5O_6S \cdot 0.75\ H_2O \cdot 0.35$ AcOEt: C 54.02(54.06), H 4.82(4.70), F 8.43 (8.31), N 10.36(10.30), S 4.74(4.47) |
| I-A-53 | ![naphthalene] | 626 | $C_{31}H_{30}F_3N_5O_6$ 0.75 $H_2O$: C 58.26 (58.34), H 4.97(5.17), F 8.92(8.77), N 10.96(10.72) |
| I-A-54 | Ph | 576 | $C_{27}H_{28}F_3N_5O_6 \cdot 0.50\ H_2O \cdot 0.25$ AcOEt: C 55.44(55.42), H 5.15(5.04), F 9.40 (9.11), N 11.55(11.64) |

TABLE 8

[Structure: R³-C(=O)-NH-CH(iPr)-C(=O)-N(pyrrolidine)-C(=O)-NH-CH(CH₂-benzothiophene)-C(=O)-CF₃]

| Compd. No. | R³ | MH⁺ | Elemental Analyses Calcd.(Found) |
|---|---|---|---|
| I-A-55 | 6-methyl-benzo[1,2,3]thiadiazol-yl | 632 | $C_{29}H_{28}F_3N_5O_4S_2 \cdot 1.10$ $H_2O \cdot 0.20$ AcOEt: C 53.49(53.52), H 4.79(4.81), F 8.52 (8.29), N 10.47(10.26), S 9.58(9.30) |
| I-A-56 | 4-methyl-quinolin-yl | 625 | $C_{32}H_{31}F_3N_4O_4S \cdot 0.50$ $H_2O \cdot 0.25$ AcOEt: C 60.45(60.23), H 5.23(5.42), F 8.69 (8.60), N 8.54(8.41), S 4.89(4.75) |
| I-A-57 | 6-methyl-benzo[1,3]dioxol-yl | 618 | $C_{30}H_{30}F_3N_3O_6S \cdot 0.50$ $H_2O$: C 57.50(57.51), H 4.99(5.13), F 9.10(8.95), N 6.71(6.55), S 5.12(4.94) |
| I-A-58 | 3-methyl-benzo[d]isoxazol-yl | 615 | $C_{30}H_{29}F_3N_4O_5S \cdot 1.00$ $H_2O$: C 56.95(56.75), H 4.94(4.80), F 9.01(8.93), N 8.86(8.58), S 5.07(4.94) |
| I-A-59 | 3-methyl-benzo[c]isoxazol-yl | 615 | $C_{30}H_{29}F_3N_4O_5S \cdot 1.25$ $H_2O$: C 56.55(56.63), H 4.98(5.02), F 8.95(8.69), N 8.79(8.77), S 5.03(4.91) |
| I-A-60 | 2,4-dimethyl-benzoxazol-yl | 629 | $C_{31}H_{31}F_3N_4O_5S \cdot 0.50$ $H_2O$: C 58.39(58.36), H 5.06(5.19), F 8.94(8.85), N 8.79(8.89), S 5.03(4.84) |
| I-A-61 | 2-methyl-benzoxazol-yl | 615 | $C_{30}H_{29}F_3N_4O_5S \cdot 1.00$ $H_2O$: C 56.95(57.10), H 4.94(4.95), F 9.01(8.84), N 8.86(8.59), S 5.07(4.91) |
| I-A-62 | 2-methyl-quinolin-yl | 625 | $C_{32}H_{31}F_3N_4O_4S \cdot 0.50$ $H_2O$: C 60.65(60.35), H 5.09(5.25), F 8.99(8.74), N 8.84(8.60), S 5.06(4.85) |

TABLE 9

| Compd. No. | R³ | R¹ | MH⁺ | Elemental Analyses Calcd.(Found) |
|---|---|---|---|---|
| I-A-63 | 3-methylfuran | 2-naphthyl | 558 | $C_{29}H_{30}F_3N_3O_5 \cdot 1.00\ H_2O$: C 60.52(60.76), H 5.60(5.53), F 9.90(9.90), N 7.30(7.04) |
| I-A-64 | 3-methylfuran | 3-benzothienyl | 564 | $C_{27}H_{28}F_3N_3O_5S \cdot 0.50\ H_2O$: C 56.64(56.66), H 5.10 (5.08), F 9.95(9.68), N 7.34 (7.14), S 5.06(5.39) |
| I-A-65 | 2,4-dimethylthiazol-5-yl | 3-benzothienyl | 609 | $C_{28}H_{31}F_3N_4O_4S_2 \cdot 1.25\ H_2O$: C 53.28(53.07), H 5.35(5.49), F 9.03(9.10), N 8.88(8.75), S 10.16(10.25) |
| I-A-66 | 4-pyridyl | 3-benzothienyl | 575 | $C_{28}H_{29}F_3N_4O_4S \cdot 0.75\ H_2O$: C 57.18(57.43), H 5.23(5.30), F 9.69(9.40), N 9.53(9.27), S 5.45(5.22) |
| I-A-67 | 2-pyridyl | 3-benzothienyl | 575 | $C_{28}H_{29}F_3N_4O_4S \cdot 1.00\ H_2O$: C 56.75(56.83), H 5.27(5.38), F 9.62(9.36), N 9.45(9.36), S 5.41(5.19) |
| I-A-68 | 5-methyl-4-phenyl-1,2,3-thiadiazol-yl | 3-benzothienyl | 658 | $C_{31}H_{30}F_3N_5O_4S_2 \cdot 1.00\ H_2O$: C 55.10(55.36), H 4.77(4.69), F 8.43(8.22), N 10.36 (10.06), S 9.49(9.36) |
| I-A-69 | 2,4-dimethyloxazol-5-yl | 3-benzothienyl | 593 | $C_{28}H_{31}F_3N_4O_5S \cdot 1.00\ H_2O$: C 55.07(55.07), H 5.45(5.52), F 9.33(9.16), N 9.17(8.90), S 5.25(5.08) |
| I-A-70 | 2-thienyl | 3-benzothienyl | 580 | $C_{27}H_{28}F_3N_3O_4S_2 \cdot 0.25 H_2O$: C 55.51(55.40), H 4.92(5.07), F 9.76(9.62), N 7.19(7.39), S 10.98(10.76) |
| I-A-71 | isoxazolo[4,5-b]pyridin-3-yl | 3-benzothienyl | 616 | $C_{29}H_{28}F_3N_5O_5S \cdot 0.80\ H_2O \cdot 0.10$ AcOEt: C 55.27(55.43), H 4.80(4.88), F 8.92(8.63), N 10.96(10.80), S 5.02(4.80) |
| I-A-72 | 3-thienyl | 3-benzothienyl | 580 | $C_{27}H_{28}F_3N_3O_4S_2 \cdot 0.75\ H_2O$: C 54.67(54.61), H 5.01(5.11), F 9.61(9.43), N 7.08(6.93), S 10.81(10.60) |

TABLE 9-continued

| Compd. No. | R³ | R¹ | MH⁺ | Elemental Analyses Calcd.(Found) |
|---|---|---|---|---|
| I-A-73 | 3-methyl-2-(phenoxy)pyridin-yl | 3-methylbenzothiophen-2-yl | 667 | $C_{34}H_{33}F_3N_4O_5S \cdot 1.00\ H_2O$: C 59.64(59.44), H 5.15(5.26), F 8.32(8.41), N 8.18(8.14), S 4.68(4.66) |
| I-A-74 | furan-2-yl | 3-methylbenzothiophen-2-yl | 564 | $C_{27}H_{28}F_3N_3O_5S \cdot 0.50\ H_2O$: C 56.64(56.73), H 5.10(5.12), F 9.95(9.89), N 7.34(7.52), S 5.60(5.42) |
| I-A-75 | 4,5-dichloro-3-methylisothiazol-yl | 3-methylbenzothiophen-2-yl | 649 | $C_{26}H_{25}Cl_2F_3N_4O_4S_2 \cdot 0.50\ H_2O$: C 47.42(47.19), H 3.98(3.98), Cl 10.77(10.86), F 8.65(8.59), N 8.51(8.30), S 9.74(9.83) |
| I-A-76 | 2,4,5-trimethyloxazol-yl | Ph | 537 | $C_{26}H_{31}F_3N_4O_5 \cdot 1.00\ H_2O$: C 56.31(56.12), H 6.00(6.00), F 10.28(10.33), N 10.10(9.91) |
| I-A-77 | 3,5-dimethyl-1,2,4-oxadiazol-yl | 3-methylbenzothiophen-2-yl | 580 | $C_{26}H_{28}F_3N_5O_5S \cdot 1.25\ H_2O$: C 51.86(52.02), H 5.11(5.12), F 9.47(9.46), N 11.63(11.40), S 5.33(5.26) |
| I-A-78 | 2,4,5-trimethyloxazol-yl | 3-methylbenzothiophen-2-yl | 593 | $C_{28}H_{31}F_3N_4O_5S \cdot 1.25\ H_2O$: C 54.67(54.53), H 5.49(5.45), F 9.27(9.11), N 9.11(8.88), S 5.21(4.96) |
| I-A-79 | pyridin-2-yl | 3-methylbenzothiophen-2-yl | 575 | $C_{28}H_{29}F_3N_4O_4S \cdot 0.50\ H_2O$: C 57.62(57.51), H 5.18(5.25), F 9.77(9.61), N 9.60(9.32), S 5.49(5.28) |
| I-A-80 | 5-phenyl-1,2,4-oxadiazol-3-yl | 3-methylbenzothiophen-2-yl | 642 | $C_{31}H_{30}F_3N_5O_5S \cdot 0.50\ H_2O$: C 57.22(56.98), H 4.80(4.88), F 8.76(8.68), N 10.76(10.53), S 4.93(4.88) |

TABLE 9-continued

[Structure: R³—C(O)—NH—CH(iPr)—C(O)—N(pyrrolidine)—C(O)—NH—CH(CH₂—R¹)—C(O)—CF₃]

| Compd. No. | R³ | R¹ | MH⁺ | Elemental Analyses Calcd.(Found) |
|---|---|---|---|---|
| I-A-81 | 1,3,5-trimethylpyrazol-4-yl | 3-methylbenzothiophen-2-yl | 592 | $C_{28}H_{32}F_3N_5O_4S$·1.25 $H_2O$·0.10 AcOEt: C 54.75(54.77), H 5.71(5.70), F 9.15(8.85), N 11.24(11.00), S 5.15(4.89) |
| I-A-82 | 2-methyl-4-methylthiazol-5-yl | 3-methylbenzothiophen-2-yl | 595 | $C_{27}H_{29}F_3N_4O_4S_2$·0.75 $H_2O$: C 53.32(53.40), H 5.05(5.06), F 9.37(9.45), N 9.21(9.15), S 10.54(10.62) |

TABLE 10

[Structure: R³ᶜ—N(imidazolidinone)—CH₂—C(O)—NH—CH(iPr)—C(O)—N(pyrrolidine)—C(O)—NH—CH(CH₂—R¹)—C(O)—CF₃]

| Compd. No. | R³ᶜ | R¹ | MH⁺ | Elemental Analyses Calcd.(Found) |
|---|---|---|---|---|
| I-A-83 | HOOC—CH₂— | 6-methylnaphthalen-2-yl | 648 | $C_{31}H_{36}F_3N_5O_7$·1.40 $H_2O$·0.20 AcOEt: C 55.32(55.47), H 5.90(5.90), F 8.25(8.09), N 10.14(9.85) |
| I-A-84 | (CH₃)₃C—OCOCH₂— | 6-methylnaphthalen-2-yl | 704 LSIMS | $C_{35}H_{44}F_3N_5O_7$·1.25 $H_2O$: C 57.88(57.89), H 6.45(6.37), F 7.85(7.65), N 9.64(9.48) |
| I-A-85 | HOOC—CH₂— | 2-methylbenzothiophen-5-yl | 654 | $C_{29}H_{34}F_3N_5O_7S$·1.35 $H_2O$·0.25 AcOEt: C 51.47(51.68), H 5.57(5.57), F 8.14(8.03), N 10.00(9.71), S 4.58(4.40) |
| I-A-86 | (CH₃)₃C—OCOCH₂— | 2-methylbenzothiophen-5-yl | 710 LSIMS | $C_{33}H_{42}F_3N_5O_7S$·1.05 $H_2O$·0.20 AcOEt: C 54.40(54.62), H 6.17(6.13), F 7.64(7.35), N 9.38(9.52), S 4.30(4.16) |
| I-A-87 | Ph—CH₂— | 2-methylbenzothiophen-5-yl | 686 LSIMS | $C_{34}H_{38}F_3N_5O_5S$·1.00 $H_2O$: C 58.03(57.95), H 5.73(5.70), F 8.10(7.99), N 9.95(9.79), S 4.56(4.39) |

TABLE 11

[Structure: pyrimidinedione-CH2-C(O)-NH-CH(R2)-C(O)-N(pyrrolidine)-C(O)-NH-CH(CH2-R1)-C(O)-CF3, with R3c on pyrimidine N]

| Comp. No. | R3c | R2 | R1 | MH+ | Elemental Analyses Calcd.(Found) |
|---|---|---|---|---|---|
| I-A-88 | HOOC—CH2— | iPr (Me,Me-CH) | Ph | 624 | |
| I-A-89 | HOOC—CH2— | iPr (Me,Me-CH) | 4-Cl—Ph | 658 LSIMS | C28H31ClF3N5O8·1.75H2O: C 48.77(48.56), H 5.04 (4.83), Cl 5.14(5.08), F 8.27(8.16), N 10.16 (10.04) |
| I-A-90 | (CH3)3C—OCOCH2— | iPr (Me,Me-CH) | 4-Cl—Ph | 658 [MH—tBu]+ LSIMS | C32H39ClF3N5O8·0.75H2O: C 52.82(52.54), H 5.61 (5.70), Cl 4.87(4.81), F 7.83(7.72), N 9.62(9.39) |
| I-A-91 | HOOC—CH2— | cyclohexyl | Ph | 678 | C32H38F3N5O8·0.40H2O·0.20 AcOEt: C 56.08 (55.85), H 5.80(5.71), F 8.11(8.04), N 9.97(9.73) |
| I-A-92 | (CH3)3C—OCOCH2— | cyclohexyl | Ph | 734 LSIMS | C36H46F3N5O8·0.75H2O: C 57.86(57.79), H 6.41 (6.50), F 7.63(7.57), N 9.37(9.08) |

TABLE 12

[Structure: R3-C(O)-NH-CH(iPr)-C(O)-N(pyrrolidine)-C(O)-NH-CH(CH2-R1)-C(O)-CF3]

| No. | R3 | R1 | MH+ | Elemental Analyses calcd.(found) |
|---|---|---|---|---|
| I-A-93 | 1-Et-3-Bn-5-Me-pyrimidine-2,4-dione | 2-methylbenzothiophene | 726 LSIMS | C36H38F3N5O6S·1.5H2O: C 57.44(57.73), H 549 (5.59), F 7.57(7.38), N 9.30(9.02), S 4.26(4.03) |
| I-A-94 | 3,4-dimethyl-5-methylisothiazole | 2-methylbenzothiophene | 609 | C28H31F3N4O4S2·0.75H2O: C 54.05(54.14), H 5.26 (5.14), F 9.16(9.05), N 9.00(8.76), S 10.31 (10.20) |

TABLE 12-continued

| | | | |
|---|---|---|---|
| I-A-95 | 4-methyl-2,1,3-benzoxadiazole | 2-methylbenzothiophene | 616 LSIMS; C$_{29}$H$_{28}$F$_3$N$_5$O$_5$S·0.90 H$_2$O·0.15 AcOEt: C 55.12 (55.22), H 4.84(4.88), F 8.84(8.55), N 10.86 (10.68), S 4.97(4.76) |
| I-A-96 | 4,5-dimethyl-1,2,3-thiadiazole | toluene | 540; C$_{24}$H$_{28}$F$_3$N$_5$O$_4$S: C 53.42 (53.42), H 5.23(5.19), F 10.56(10.45), N 12.98 (12.92), S 5.94(5.86) |
| I-A-97 | 4,5-dimethyl-1,2,3-thiadiazole | 2-methylbenzothiophene | 596; C$_{26}$H$_{28}$F$_3$N$_5$O$_4$S$_2$·0.5 H$_2$O: C 51.65(51.51), H 4.83 (4.89), F 9.43(9.21), N 11.58(11.33), S 10.61 (10.47) |
| I-A-98 | 3,4-dimethyl-5-methylisoxazole | 2-methylbenzothiophene | 593; C$_{28}$H$_{31}$F$_3$N$_4$O$_5$S·1.00 H$_2$O: C 55.07(55.33), H 5.45 (5.37), F 9.33(9.03), N 9.17(9.09), S 5.25(5.01) |
| I-A-99 | 4-methyl-5-methyl-1,2,3-thiadiazole | 2-methylbenzothiophene | 596; C$_{26}$H$_{28}$F$_3$N$_5$O$_4$S$_2$·0.75H$_2$O: C 51.26(51.06), H 4.88(4.84), F 9.36(9.11), N 11.50(11.31), S 10.53(10.47) |
| I-A-100 | 3,5-dimethyl-1,2,4-thiadiazole | 2-methylbenzothiophene | 596; C$_{26}$H$_{28}$F$_3$N$_5$O$_4$S$_2$·0.50 H$_2$O: C 51.65(51.66), H 4.83(4.81), F 9.43(9.35), N 11.58(11.41), S 10.61(10.41) |
| I-A-101 | 3,4-dimethyl-5-methylisoxazole | cyclopropyl | 501; C$_{23}$H$_{31}$F$_3$N$_4$O$_5$·0.25 H$_2$O: C 54.70(54.44), H 6.29(6.15), F 11.29(11.19), N 11.09(10.94) |
| I-A-102 | 4,7-dimethyl-2-(2-methylpropan-2-yl)benzoxazole | 2-methylbenzothiophene | 685 LSIMS; C$_{35}$H$_{39}$F$_3$N$_4$O$_5$S·1.25H$_2$O: C 59.44(59.50), H 5.91(5.85), F 8.06(7.91), N 7.92(7.82), S 4.53(4.34) |
| I-A-103 | 3-methyl-5-phenyl-1,2,4-thiadiazole | 2-methylbenzothiophene | 658 LSIMS; C$_{31}$H$_{30}$F$_3$N$_5$O$_4$S·0.50 H$_2$O: C 55.84(55.85), H 4.69(4.74), F 8.55(8.33), N 10.50(10.36), S 9.62(9.45) |
| I-A-104 | 1-benzyl-3-methylimidazolidin-2-one | 2-methylbenzothiophene | 700 LSIMS |

Reference Example 9

Preparation of Reference Compound (A) Disclosed in WO-A-93/25574

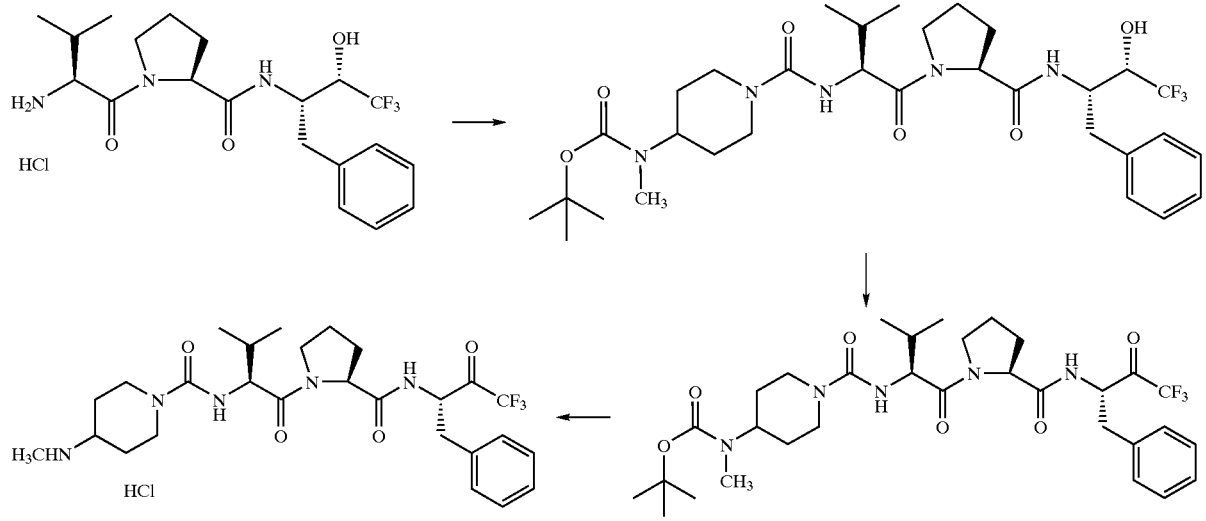

A. {(2S)-1-[(2S)-2-({4-[(tert-butoxy)-N-methylcarbonylamino]piperidyl}carbonylamino)-3-methylbutanoyl]pyrrolidin-2-yl}-N-[(1S,2S)-3,3,3-trifluoro-2-hydroxy-1-benzylpropyl]carboxamide:

A solution of [(2S)-1-((2S)-2-amino-3-methylbutanoyl) pyrrolidin-2-yl]-N-[(1S,2S)-3,3,3-trifluoro-2-hydroxy-1-benzylpropyl]carboxamide hydrochloride (2.7 g, 6.03 mmol) and triethylamine (0.67 g, 6.63 mmol) in dichloromethane (15 ml) was added to a stirred 0–5° C. slurry of carbonyldiimidazole (1.1 g, 6.63 mmol) and imidazole (0.82 g, 12.1 mmol) in dichloromethane (30 ml) and the resulting mixture was stirred at 25° C. for 30 min. A solution of 4-[N-[(1,1-dimethylethoxy)carbonyl]methylamino] piperidine (1.3 g, 6.03 mmol) in dichloromethane (10 ml) was added and the mixture stirred at 25° C. for 2 days. The resulting solution was washed with 5% aqueous potassium hydrogen sulfate solution, saturated aqueous sodium hydrogen carbonate solution and brine. The organic solution was dried over sodium sulfate, filtered and evaporated under reduced pressure. The residue was subjected to column chromatography on CHP20P, and eluted with a gradient of 20 to 70% acetonitrile in water under a medium pressure to give the title compound (1.0 g, yield; 25%).

$^1$H NMR (300 MHz, CDCl$_3$): δ 0.96–0.98 (3H, d, J=6.8 Hz), 1.00–1.02 (3H, d, J=6.6 Hz), 1.46 (9H, s), 1.57–1.77 (7H, m), 1.84–1.90 (1H, m), 2.36–2.42 (1H, m), 2.72 (3H, s), 2.90–3.06 (4H, m), 3.13–3.20 (1H, m), 3.43–3.53 (1H, m), 3.84–4.05 (5H, m), 4.35–4.38 (1H, d, J=7.3 Hz), 4.85–4.90 (2H, m), 6.08–6.12 (1H, d, J=11.7 Hz), 7.19–7.30 (5H, m), 7.78–7.81 (1H, d, J=9.9 Hz)

APCI-MS: 656 (MH$^+$)

B. {(2S)-1-[(2S)-2-({4-[(tert-butoxy)-N-methylcarbonylamino]piperidyl}carbonylamino)-3-methylbutanoyl]pyrrolidin-2-yl}-N-[(1S,2S)-3,3,3-trifluoro-2-oxo-1-benzylpropyl]carboxamide:

To a solution of {(2S)-1-[(2S)-2-({4-[(tert-butoxy)-N-methylcarbonylamino]piperidyl}carbonylamino)-3-methylbutanoyl]pyrrolidin-2-yl-N-[(1S,2S)-3,3,3-trifluoro-2-hydroxy-1-benzylpropyl]carboxamide (1.0 g, (1.52 mmol) in dichloromethane (10 ml) were added tert-butyl alcohol (0.15 ml, 1.52 mmol) and Dess-Martin periodinane (1.3 g, 3.05 mmol). The reaction mixture was stirred at room temperature for 1 hour and then the solvent was removed under reduced pressure. The residue was extracted with ethyl acetate and then washed with saturated aqueous sodium thiosulfate solution, saturated aqueous sodium hydrogen carbonate solution and brine. The organic solution was dried over sodium sulfate, filtered and evaporated under reduced pressure. The residue was subjected to column chromatography on CHP20P, and eluted with a gradient of 30 to 70% acetonitrile in water under a medium pressure to give the title compound (0.8 g, yield; 81%).

$^1$H NMR (300 MHz, CDCl$_3$): δ 0.94–0.96 (3H, d, J=6.8 Hz), 0.99–1.01 (3H, d, J=6.6 Hz), 1.47 (9H, s), 1.56–1.86 (7H, m), 2.11–2.17 (1H, m), 2.73 (3H, s), 2.76–3.05 (4H, m), 3.28–3.36 (1H, m), 3.85–4.13 (4H, m), 4.36–4.39 (1H, d, J=8.1 Hz), 4.65 (1H, m), 4.82–4.85 (1H, d, J=7.9 Hz), 5.76 (1H, s), 6.16 (1H, s), 7.14–7.31 (5H, m), 7.37–7.40 (1H, d, J=9.0 Hz)

APCI-MS: 654 (MH$^+$)

C. [(2S)-1-((2S)-3-methyl-2-{[4-(methylamino)piperidyl] carbonylamino}butanoyl)pyrrolidin-2-yl]-N-[(1S)-3,3,3-trifluoro-2-oxo-1-benzylpropyl]carboxamide hydrochloride:

To {(2S)-1-[(2S)-2-({4-[(tert-butoxy)-N-methylcarbonylamino]-piperidyl}carbonylamino)-3-methylbutanoyl]pyrrolidin-2-yl-N-[(1S,2S)-3,3,3-trifluoro-2-oxo-1-benzylpropyl]carboxamide (0.5 g, 0.77 mmol) was added 4N-hydrogenchloride in 1,4-dioxane solution (10 ml). After stirring at 0–5° C. for 1 hour, the solvent was removed under reduced pressure. The residue was treated with isopropyl alcohol and evaporated under reduced pressure to give the title compound (0.35 g, yield; 78%).

$^1$H NMR (300 MHz, d$_6$-DMSO): δ 0.87–0.89 (3H, d), 0.89–0.93 (3H, d), 1.32–1.39 (3H, m), 1.63–1.76 (2H, m), 1.93–1.96 (3H, m), 2.52 (3H, s), 2.61–2.73 (2H, m), 3.11–3.15 (2H, m), 3.37–3.39 (1H, m), 3.86 (4H, m), 4.04–4.37 (4H, m), 6.48–6.50 (1H, d, J=8.1 Hz), 7.12–7.24 (5H, m), 7.79–7.82 (1H, d, J=9.3 Hz), 8.93 (1H, m)

APCI-MS: 554 (MH$^+$)

Elemental Analysis: $C_{27}H_{38}F_3N_5O_4$·1.25 HCl·1.50 H$_2$O·0.50 dioxane Calcd.: C 51.97, H 6.96, F 8.50, N 10.45, Cl 6.61 Found: C 51.99, H 7.23, F 8.23, N 10.23, Cl 6.66

PHARMACOLOGICAL PROPERTIES

The pharmacological properties of the present compounds (I-A) are explained below.

The present compounds (I-A) exhibit an excellent chymase inhibitory activity as seen in Experiment 1 and can be used in the treatment of various diseases including allergic conditions in which mast cells play a main role. In these allergic conditions, acceleration of vascular permeability following mast cells degranulation causes inflammatory reactions by inducing inflammatory cells infiltration as well as immune complexes deposition in the vascular walls.

As shown in Experiment 2, the present compounds (I-A) inhibit the acceleration of vascular permeability induced by chymase, resulting in a suppression of skin inflammation. This finding suggests that the present compounds (I-A) are useful as skin anti-inflammatory agents.

In addition to the properties mentioned above, the present compounds (I-A) sustain high levels in the plasma even after oral administration and exhibit low toxicity (Experiments 3 and 4). Combining the pharmacological properties above, it is believed the present compounds (I-A) are useful as medicaments.

PHARMACOLOGICAL EXPERIMENTS

Experiment 1

Chymase Inhibitory Activity ($IC_{50}$)

The inhibitory activities of the compounds on monkey chymase and human chymase were tested in vitro. The test compounds are as shown by Compound Nos. in Tables 13 and 14.

Preparation of Monkey Chymase

Chymase was purified from monkey cheek pouch and stomach in the following manner.

Briefly, chymase was extracted from homogenized monkey cheek pouch and stomach with 0.01 mol/1000 ml sodium phosphate buffer, pH 7.4, containing 2 mol/1000 ml KCl and 0.1% Nonidet P-40 (Amresco Inc.). The solution containing chymase was applied to a heparin actigel column, and the chymase-rich fractions were collected.

Preparation of Human Chymase

Human chymase was produced in mammalian cells using a recombinant DNA technique.

Construction of a human prochymase expression plasmid was performed in the following manner. Briefly, single stranded cDNA was synthesized from human heart mRNA (Clontech Laboratories, Inc.). Polymerase chain reaction amplification was carried out using the cDNA as a template and appropriate pairs of primers. The primer sequences were determined based on the human preprochymase. The amplified product was cloned into the plasmid pUC18, and then recloned into the plasmid pBluescript II KS(+) (Stratagene). Finally, the DNA fragment carrying the entire protein-coding sequences of the human preprochymase was inserted to a transient expression vector by the usual method to yield the human prochymase expression plasmid.

Transfection of COS7 cells with the human prochymase expression plasmid was carried out using the FuGene™ 6 transfection reagent (Boehringer Mannheim). About 7 hours after exposure to DNA, the culture medium was changed to a serum-free one. The culture supernatant was collected after 2 days culture.

Human prochymase was purified from the culture supernatant using a heparin actigel column as described above in the preparation of monkey chymase.

In order to produce active chymase, the human prochymase was incubated with dipeptidylpeptidase I (Sigma). The resultant active human chymase was purified using a heparin actigel column as described above. The active human chymase was eluted with 0.01 mol/1000 ml sodium phosphate buffer pH 7.4 containing 2 mol/1000 ml NaCl.

Measurement of Chymase Inhibitory Activity (In Vitro Assay)

The chymase inhibitory activities of compounds I-A of this invention were measured according to the following method. Briefly, the purified monkey or human chymase was diluted to an appropriate concentration with 0.01 mol/1000 ml sodium phosphate buffer, pH 7.4, containing 2 mol/1000 ml KCl and 0.1% Nonidet P-40 and used as enzyme solution. Angiotensin I (Peptide Institute Inc.) was diluted with water to 5 mg/ml and used as substrate solution. Test compounds were serially diluted with 10% DMSO. Ten µl of the enzyme solution and 10 µl of the diluted test compound were mixed with 60 µl of 0.1 mol/1000 ml sodium phosphate buffer, pH 7.4, and kept at room temperature. After pre-incubation of the mixture at 37° C., 20 µl of the substrate solution was added to the enzyme-test compound mixture and the new mixture was incubated at 37° C. Fifty µl of 30% trichloroacetic acid solution was finally added to stop the enzymatic reaction.

The amount of L-His-L-Leu was measured as angiotensin II produced by the enzymatic reaction. Briefly, 10 µl of the reaction mixture and 10 µl of 1% orthophthalaldehyde solution dissolved in methanol were mixed with 100 µl of 2 mol/1000 ml NaOH and kept at room temperature. The reaction was then stopped by adding 10 µl of 6 mol/1000 ml HCl. Finally, the fluorescence induced by the reaction was measured using in a photometer with an excitation wavelength of 355 nm and an emission wavelength of 460 nm. Chymase inhibitory activities of test compounds were expressed as 50% inhibitory concentration ($IC_{50}$).

Results

The chymase inhibitory activities of the compounds of the present invention are shown in Table 13 as to inhibitory activity on monkey chymase and in Table 14 as to the inhibitory activity on human chymase.

TABLE 13

Monkey Chymase inhibitory activity

| Compound Nos. | Monkey Chymase Inhibition ($IC_{50}$:nM) |
|---|---|
| I-A-1 | 3.8 |
| I-A-2 | 54 |
| I-A-3 | 9.3 |
| I-A-4 | 12 |
| I-A-5 | 16 |
| I-A-6 | 33 |
| I-A-7 | 34 |
| I-A-8 | 48 |
| I-A-9 | 61 |
| I-A-10 | 77 |
| I-A-13 | 50 |
| I-A-14 | 59 |
| I-A-15 | 82 |
| I-A-16 | 110 |
| I-A-17 | 140 |
| I-A-18 | 220 |
| I-A-20 | 5.1 |
| I-A-21 | 19 |
| I-A-22 | 37 |
| I-A-23 | 50 |
| I-A-24 | 150 |
| I-A-26 | 44 |
| I-A-27 | 51 |
| I-A-28 | 54 |
| I-A-29 | 57 |

TABLE 13-continued

Monkey Chymase inhibitory activity

| Compound Nos. | Monkey Chymase Inhibition (IC$_{50}$:nM) |
| --- | --- |
| I-A-30 | 65 |
| I-A-31 | 68 |
| I-A-32 | 73 |
| I-A-33 | 73 |
| I-A-34 | 76 |
| I-A-35 | 80 |
| I-A-36 | 89 |
| I-A-37 | 95 |
| I-A-38 | 110 |
| I-A-39 | 120 |
| I-A-40 | 120 |
| I-A-41 | 120 |
| I-A-42 | 130 |
| I-A-43 | 140 |
| I-A-44 | 150 |
| I-A-45 | 170 |
| I-A-46 | 170 |
| I-A-47 | 350 |
| I-A-52 | 31 |
| I-A-53 | 31 |
| I-A-54 | 42 |
| I-A-55 | 63 |
| I-A-56 | 47 |
| I-A-57 | 100 |
| I-A-58 | 210 |
| I-A-59 | 250 |
| I-A-60 | 430 |
| I-A-63 | 150 |
| I-A-64 | 73 |
| I-A-65 | 37 |
| I-A-66 | 49 |
| I-A-67 | 94 |
| I-A-68 | 27 |
| I-A-69 | 98 |
| I-A-70 | 140 |
| I-A-71 | 140 |
| I-A-72 | 160 |
| I-A-73 | 300 |
| I-A-74 | 350 |
| I-A-75 | 380 |
| I-A-83 | 61 |
| I-A-84 | 190 |
| I-A-85 | 75 |
| I-A-86 | 210 |
| I-A-87 | 250 |
| I-A-88 | 68 |
| I-A-89 | 150 |
| I-A-90 | 280 |
| I-A-91 | 150 |
| I-A-92 | 860 |
| I-A-93 | 200 |
| I-A-94 | 15 |
| I-A-95 | 47 |
| I-A-96 | 50 |
| I-A-97 | 59 |
| I-A-98 | 63 |
| I-A-99 | 83 |
| I-A-100 | 260 |
| Reference compound (A) | 1600 |

TABLE 14

Human Chymase inhibitory activity

| Compound Nos. | Human Chymase Inhibition (IC$_{50}$:nM) |
| --- | --- |
| I-A-1 | 55 |
| I-A-2 | 83 |
| I-A-3 | 50 |
| I-A-4 | 57 |

TABLE 14-continued

Human Chymase inhibitory activity

| Compound Nos. | Human Chymase Inhibition (IC$_{50}$:nM) |
| --- | --- |
| I-A-5 | 83 |
| I-A-20 | 36 |
| I-A-52 | 57 |
| I-A-53 | 69 |
| I-A-54 | 90 |
| I-A-63 | 92 |
| I-A-64 | 96 |
| I-A-95 | 95 |
| I-A-96 | 77 |
| I-A-97 | 75 |
| Reference compound (A) | 1200 |

As is shown in Tables 13 and 14, the compounds of the present invention showed excellent inhibitory activities on both of monkey chymase and human chymase. On the other hand, Reference Compound (A), which is disclosed in Example 28 of WO-A-93/25574, has a very low chymase inhibitory activity.

Experiment 2

Inhibition of Vascular Permeability

Experiment 2 was carried out using a dye as maker in order to prove that the acceleration of vascular permeability induced by chymase is inhibited by the administration of the present compounds.

Skin Permeability Test

Skin permeability test was carried out according to the following method. Briefly, male Hartley guinea pigs (350–460 g, Shizuoka Laboratory Animal Center, Japan) were anesthetized by intraperitoneal injection of Nembutal™ (30 mg/kg; Dainippon Pharmaceutical Co., Ltd., Japan). After shaving the guinea pigs dorsa, 50 µl of purified human chymase (Elastin Products Inc., USA) diluted with phosphate buffered saline (PBS) to a concentration of 1.8 units /55 µg protein/ml (1 unit of chymase represents the amount of chymase required to hydrolyze 1.0 µmole of N-benzoyl-L-tyrosine-ethyl ester (BTEE) per minute at 25° C.; pH 7.8) were injected intradermally into three dorsal sites of each animal. Solvent (0.05 mol/1000 ml sodium acetate and 1 mol/1000 ml sodium chloride mixture diluted with PBS) was injected similarly into three other dorsal sites of the same animal. Following the final injection, 1% (w/v) Evans Blue dye in saline (0.4 ml/100 g body weight) was injected intravenously into the saphenous vein. The animals were killed 30 minutes thereafter by exsanguination under anesthesia, and their dorsal skins were removed. The amounts of dye leakage into the dorsal skins were measured according to the following method.

Briefly, the area around each injection site (16 mm diameter) was punched out from the inside of the skin, and the leaked dye was extracted by incubation of the punched skin in N,N-dimethylformamide (DMF, 3 ml) at 55° C. overnight. The absorbance of the dye extract was then measured using a spectrophotometer at a wavelength of 620 nm. To measure the amount of dye leakage into the dorsal skin, the calibration curve was obtained from external standards of Evans Blue dye as follows: Evan's Blue dye (3.75–30 µg) was added into the control skin in DMF (3 ml). Control skins were treated in the same manner as the punched skins, and their dye extracts were used as external standards. The amount of chymase-induced dye leakage (ACDL) and the amount of solvent-induced dye leakage (ASDL) in each animal were calculated as the average of dye leakage from the three treated dorsal sites in each case.

Treatment with Test-Compounds

Animals were orally administrated 0.5% tragacanth or test-compounds (100 mg/kg) suspended in 0.5% tragacanth solution 1 hour before intradermal injection of human chymase. Test-compounds inhibition rate of chymase-induced dye leakage was calculated using the following formula:

Dye leakage inhibition rate (%)={(A−B)−(C−D)}/(A−B)×100

A: ACDL in tragacanth-treated group
B: ASDL in tragacanth-treated group
C: ACDL in test-compound-treated group
D: ASDL in test-compound-treated group Results Test-compounds (I-A-1) and (I-A-20) significantly inhibited the dye leakage by 34% and 59%, respectively.

Experiment 3

Plasma Level

Plasma levels of test compounds were measured in the following manner.

Briefly, test compounds were dissolved in DMSO to 100 mg/ml, and suspended with 0.5% tragacanth solution 1 mg/ml. Male ddy mice, weighing about 30 g, were orally administered the test compound solution. After one hour, blood was collected from the heart under anesthesia with Nembutal (Dainippon Pharmaceutical Co., Ltd.) and centrifuged to obtain plasma. The collected plasma (125 $\mu$l) was mixed with 10% DMSO (120 $\mu$l) and ethyl acetate (720 $\mu$l). After centrifugation, the ethyl acetate layer was collected and evaporated. The residue was dissolved and diluted serially as test samples with 10% DMSO. Chymase inhibitory activities of test samples were measured in the same manner as described in Experiment 1. In this chymase inhibitory assay of test samples, 0.1 mol/1000 ml sodium phosphate buffer, pH 7.4 contained 5 mmol/1000 ml ethylenediaminetetraacetic acid (EDTA) disodium salt, 0.77 mmol/1000 ml diisopropyl fluorophosphate (DFP) and 8 mmol/1000 ml dipyridyl. Plasma concentrations of test compounds were calculated from calibration curves.

The calibration curve was obtained in the following manner. Test compounds (0.06–60 ng) were added into the control plasma. The control plasma was treated in the same manner as for test samples. Finally, chymase inhibitory activities of the 10% DMSO-dissolved residues were measured and plotted against the amount of test compounds.

Results

The results are shown in Table 15.

TABLE 15

| Plasma level | |
|---|---|
| Compound Nos. | Plasma Level ($\mu$g/ml) |
| I-A-1 | 0.48 |
| I-A-2 | 2.7 |
| I-A-3 | 0.32 |
| I-A-4 | 0.94 |
| I-A-5 | 0.63 |
| I-A-20 | 0.57 |

As is shown in Table 15, the compounds of the present invention showed high blood levels even by oral administration.

Experiment 4

Toxicity Study

Five-week-old male ddy mice were administered orally once a day for 2 weeks with the compound I-A-1 at dose levels of 30 and 300 mg/kg/day. In these mice, there was no treatment-related finding observed in any of parameters including body weight, diet consumption, heart weight, liver weight, kidney weight, necropsy finding, hematology, and blood chemistry.

As is clear from the above experimental results, the compounds of the present invention are an excellent chymase inhibitor and are useful for the treatment of various diseases in which chymase participates.

The compounds of the present invention can be administered orally, parenterally, dermally/trans dermally, ocularly, etc., but preferably oral rout. The dose of the compounds may vary depending on the administration routes, severity of diseases, and body weight and age of the patients, etc. For example, when the present compounds are administered orally, the dose thereof is usually in the range of about 0.5 to about 5000 mg/60 kg of body weight per day, preferably about 5 to about 2000 mg/60 kg of body weight per day, most preferably 15 to 300 mg/60 kg of body weight per day. When the present compounds are administered in the form of a drop preparation, the dose thereof is usually in the range of 0.06 to 30 mg, preferably in the range of 0.3 to 6 mg/60 kg of body weight per day.

The compounds of the present invention are used in the form of a conventional pharmaceutical preparation. Such pharmaceutical preparations include tablets, capsules, granules, fine granules, powders aqueous or oily liquids, ointments and the like. These pharmaceutical preparations may be prepared in the usual manner using conventional pharmaceutically acceptable components. Any components can be used so long as they do not react with the compounds (I-A) of the present invention.

Concrete examples of the component in solid preparations include maize starch (i.e., corn starch), mannitol, lactose, low substituted HPC (i.e., low substituted hydroxypropylcellulose), HPC (i.e., hydroxypropylcellulose), crystalline cellulose, carboxymethylcellulose calcium, magnesium stearate, light anhydrous silicic acid, and the like. An example of the component in liquid preparations includes water for injection, soybean oil, surfactant such as sorbitan mono-oleate, Poloxamer 188 and Polysorbate 80, and the like. An example of the component in ointments preparation includes white petrolatum.

The pharmaceutical preparation of the present invention will explained by Preparations. In the following Preparations, the present compounds of the active ingredient are used after being micronized to a size of 5 $\mu$m or below.

Preparations A, B and C: Tablets

The components of granule as listed in Table 16 are granulated in a conventional manner, and thereto are added external excipients, and the mixture is tabletted to give tablets weighting 120 mg to 300 mg.

TABLE 16

| | | Amount (mg) | | |
|---|---|---|---|---|
| | Components | Pre. A | Pre. B | Pre. C |
| Granule | Compound I-A-1 | 1 | 10 | 100 |
| | Lactose | 84.2 | 75.2 | 117.5 |
| | Maize starch | — | 12 | — |
| | Low substituted HPC | 12 | — | 30 |
| | HPC | 3 | 3 | 8 |
| External excipients | Crystalline cellulose | 18 | 18 | 40 |
| | Magnesium stearate | 1.2 | 1.2 | 3.0 |
| | Light anhydrous silicic acid | 0.6 | 0.6 | 1.5 |
| | Total (mg) | 120 | 120 | 300 |

Preparations D, E and F: Granules

The components of granule as listed in Table 17 are granulated in a conventional manner, and thereto are added external excipients to give granules.

TABLE 17

| | Components | Amount (wt. %) | | |
| --- | --- | --- | --- | --- |
| | | Pre. D | Pre. E | Pre. F |
| Granule | Compound I-A-1 | 1 | 10 | 50 |
| | D-Mannitol | 85.5 | 76.5 | 36.5 |
| | Low substituted HPC | 10 | 10 | 10 |
| | HPC | 3 | 3 | 3 |
| External excipient | Light anhydrous silicic acid | 0.5 | 0.5 | 0.5 |
| | Total (%) | 100 | 100 | 100 |

Preparations G and H: Aqueous Liquids

The components as listed in Table 18 are mixed uniformly in a conventional manner to give an aqueous liquid, which can be used as a drop or an injection.

TABLE 18

| | Amount (wt. %) | |
| --- | --- | --- |
| Components | Pre. G | Pre. H |
| Compound I-A-20 | 1 | 10 |
| Poloxamer 188 | 0.5 | 1 |
| Sodium chloride | 0.9 | 0.9 |
| Water for injection | q.s. | q.s. |
| Total (%) | 100 | 100 |

Preparations J, K and L: Oily Liquids

The components as listed in Table 19 are mixed uniformly in a conventional manner to give an oily liquid, which can be used as an injection, or can be filled in soft capsules and used as an oral preparation.

TABLE 19

| | Amount (wt. %) | | |
| --- | --- | --- | --- |
| Component | Pre. J | Pre. K | Pre. L |
| Compound I-A-5 | 1 | 10 | 50 |
| Soybean oil | 98.9 | 89.9 | 49.9 |
| Sorbitan mono-oleate | 0.1 | 0.1 | 0.1 |
| Total (%) | 100 | 100 | 100 |

Preparations M, N and P: Ointments

The components as listed in Table 20 are mixed uniformly in a conventional manner to give ointments, which can be used as a dermal administration preparation.

TABLE 20

| | Amount (wt. %) | | |
| --- | --- | --- | --- |
| Component | Pre. M | Pre. N | Pre. P |
| Compound I-A-1 | 10 | 20 | 30 |
| White petrolatum | 90 | 80 | 70 |
| Total (%) | 100 | 100 | 100 |

INDUSTRIAL APPLICABILITY

The compounds (I-A) of the present invention have excellent chymase inhibitory activity and are useful as chymase inhibitor for the prevention or treatment of various diseases in which chymase participates, for example, as an antiallergic and antiinflammatory agent, an antirestenosis agent, or an antiarteriosclerotic agent. The compounds (I-B) are useful as an intermediate for the preparation of said active compounds (I-A).

What is claimed is:

1. A compound of the formula (I):

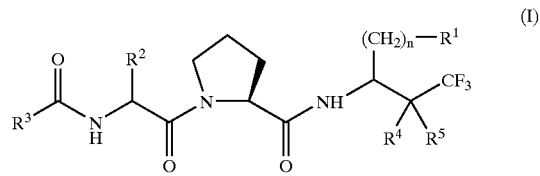

(I)

wherein $R^1$ is a cycloalkyl group, a substituted or unsubstituted phenyl group, a substituted or unsubstituted naphthyl group, a tetrahydronaphthyl group, an indanyl group, a thienyl group, a furyl group, a substituted or unsubstituted indolyl group, a substituted or unsubstituted dihydroindolyl group, a benzofuryl group, a dihydrobenzofuryl group, a substituted or unsubstituted benzothienyl group or an S-mono- or di-oxide thereof, or a dihydrobenzothienyl group, said substituted phenyl, naphthyl and benzothienyl groups having each independently one to three substituents independently selected from a halogen atom, a lower alkoxy group, a hydroxy group and a lower alkyl group having optionally one to three halogen atoms; and said substituted indolyl and dihydroindolyl groups having a substituent on (N) at the 1-position selected from a lower alkyl group and a lower alkyl-carbonyl group;

$R^2$ is a hydrogen atom, an alkyl group, a phenyl-lower alkyl group, a cycloalkyl group or a cycloalkyl-lower alkyl group;

$R^3$ is (i) a substituted or unsubstituted, unsaturated monocyclic heterocyclic group;

(ii) a substituted or unsubstituted, saturated or unsaturated monocyclic heterocyclic group which is fused by a benzene ring or a pyridine ring, wherein said substituted heterocyclic groups in (i) and (ii) each independently have one to three substituents independently selected from a halogen atom, a lower alkyl group, a lower alkoxy group, a lower alkyl-carbonyl group, a cyano group, a carboxamido group, a phenyl group and a phenoxy group; said phenyl and phenoxy substituents may further optionally have one to three substituents independently selected from a halogen atom, a lower allyl group and a halogeno-lower alkyl group; or (iii) a group of the formula (a):

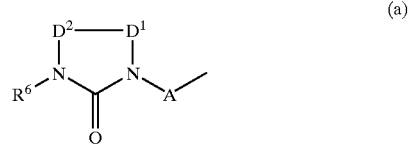

(a)

wherein A is a lower alkylene group, $D^1$ and $D^2$ are both simultaneously a methylene group or alternatively, one of $D^1$ and $D^2$ is a methylene group and another is a vinylene group where each methylene group being optionally substituted by an oxo group or a lower alkyl group, and said vinylene group being optionally substituted by a lower alkyl group; $R^6$ is a lower alkyl group substituted by a carboxyl group, a lower alkoxycarbonyl group or a phenyl group;

$R^4$ and $R^5$ are each independently a hydrogen atom or a hydroxy group, but $R^4$ and $R^5$ are not simultaneously a hydrogen atom, or both combine to form an oxo group;

n is 0, 1, 2 or 3;

or a salt thereof.

2. A compound according to claim 1, wherein $R^1$ is a $C_3$–$C_8$ cycloalkyl group, a phenyl group, a phenyl group substituted by one to three substituents independently selected from a halogen atom, a $C_1$–$C_4$ alkoxy group, a hydroxy group, a $C_1$–$C_4$ alkyl group and a halogeno-$C_1$–$C_4$ alkyl group; a naphthyl group, a tetrahydronaphthyl group, an indanyl group, a thienyl group, a furyl group, an indolyl group, an N—($C_1$–$C_4$ alkyl)indolyl group, an N—($C_1$–$C_4$ alkyl-carbonyl)indolyl group, a dihydroindolyl group, a benzofuryl group, a dihydrobenzofuryl group, a benzothienyl group or an S-mono- or di-oxide thereof, or a dihydrobenzothienyl group;

$R^2$ is a hydrogen atom, a $C_1$–$C_6$ allyl group, a phenyl-$C_1$–$C_4$ alkyl group, a $C_3$–$C_8$ cycloalkyl group or a $C_3$–$C_8$ cycloalkyl-$C_1$–$C_4$ alkyl group;

$R^3$ is (i) an unsaturated monocyclic heterocyclic group selected from furyl, thienyl, oxazolyl, isoxazolyl, thiazolyl, isothiazolyl, 1,2,3-thiadiazolyl, 1,2,4-oxadiazolyl, and pyridyl;

(ii) a benzene- or pyridine-fused saturated or unsaturated monocyclic heterocyclic group selected from benzofuryl, benzothienyl, indolyl, benzoxazolyl, benzisoxazolyl, benzothiazolyl, benzisothiazolyl, benzofurazanyl or N-oxide thereof, quinolyl, benzodioxolyl, and isoxazolo[4,3-b]pyridinyl, wherein said heterocyclic groups in (i) and (ii) may each independently have one to three substituents independently selected from a fluorine atom or chlorine atom, a $C_1$–$C_4$ alkyl group, a $C_1$–$C_4$ alkoxy group, a $C_1$–$C_4$ alkyl-carbonyl group, a cyano group, a carboxamido group, a phenyl group and a phenoxy group; said phenyl and phenoxy substituents may further optionally have one to three substituents independently selected from a halogen atom, a $C_1$–$C_4$ alkyl group and a halogeno-$C_1$–$C_4$ alkyl group; or (iii) a group of any one of the formulae (a-1) to (a-4):

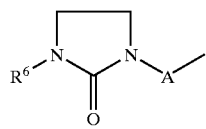

(a-1)

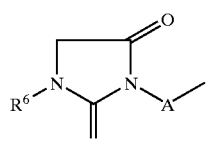

(a-2)

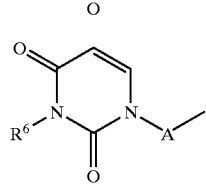

(a-3)

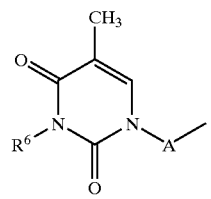

(a-4)

wherein A is a $C_1$–$C_4$ alkylene group, and $R^6$ is a $C_1$–$C_4$ alkyl group substituted by a carboxyl group, a $C_1$–$C_5$ alkoxycarbonyl group or a phenyl group;

$R^4$ and $R^5$ are each independently a hydrogen atom or a hydroxy group, but $R^4$ and $R^5$ are not simultaneously a hydrogen atom, or both combine to form an oxo group;

n is 1 or 2;

or a salt thereof.

3. A compound according to claim 2, wherein $R^1$ is a $C_5$–$C_7$ cycloalkyl group, a phenyl group, a phenyl group substituted by one to three substituents independently selected from fluorine, chlorine or bromine atom, a $C_1$–$C_4$ alkoxy group, a hydroxy group, a $C_1$–$C_4$ alkyl group and a trifluoromethyl group; a naphthyl group, a tetrahydronaphthyl group, an indanyl group, a thienyl group, a furyl group, an indolyl group, an N—($C_1$–$C_4$ alkyl)indolyl group, an N-acetylindolyl group, a dihydroindolyl group, a benzofuryl group, a dihydrobenzofuryl group, a benzothienyl group or an S-mono- or di-oxide thereof, or a dihydrobenzothienyl group;

$R^2$ is a hydrogen atom, a $C_1$–$C_4$ alkyl group, a phenyl-$C_1$–$C_2$ alkyl group, a $C_5$–$C_7$ cycloalkyl group or a $C_5$–$C_7$ cycloalkyl-$C_1$–$C_2$ alkyl group;

$R^3$ is (i) an unsaturated monocyclic heterocyclic group selected from furyl, thienyl, oxazolyl, isoxazolyl, thiazolyl, isothiazolyl, 1,2,3-thiadiazolyl, 1,2,4-oxadiazolyl, and pyridyl;

(ii) a benzene- or pyridine-fused saturated or unsaturated monocyclic heterocyclic group selected from benzoxazolyl, benzisoxazolyl, benzofurazanyl or N-oxide thereof, quinolyl, benzodioxolyl, and isoxazolo[4,3-b]pyridinyl, wherein said heterocyclic groups in (i) and (ii) may each independently have one to three substituents independently selected from a fluorine or chlorine atom, a $C_1$–$C_3$ alkyl group, a $C_1$–$C_3$ alkoxy group, an acetyl group, a cyano group, a carboxamido group, a phenyl group and a phenoxy group, said phenyl and phenoxy substituents may further optionally have one to three substituents selected from a fluorine or chlorine atom, a $C_1$–$C_3$ alkyl group and a trifluoromethyl group; or (iii) a group of any one of the formulae (a-1) to (a-4):

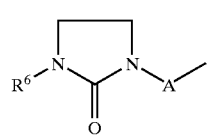

(a-1)

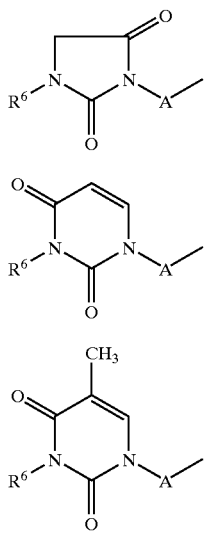

wherein A is a $C_1$–$C_2$ alkylene group, and $R^6$ is a $C_1$–$C_2$ alkyl group substituted by a carboxyl group, a tert-butoxycarbonyl group or a phenyl group;

$R^4$ and $R^5$ are each independently a hydrogen atom or a hydroxy group, but $R^4$ and $R^5$ are not simultaneously a hydrogen atom, or both combines to form an oxo group;

n is 1 or 2;

or a salt thereof.

4. A compound of the formula (I-A):

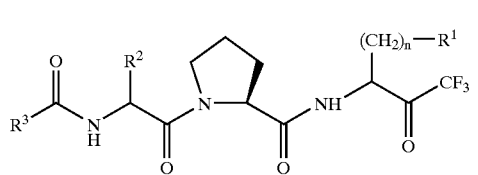

wherein $R^1$, $R^2$, $R^3$ and n are as defined in claim 1.

5. A compound according to claim 4, wherein $R^1$, $R^2$, $R^3$ and n are as defined above.

6. A compound according to claim 4, wherein $R^1$, $R^2$, $R^3$ and n are as defined above.

7. A compound of the formula (I-A'):

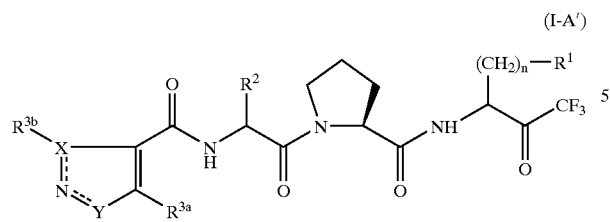

wherein $R^{3a}$ and $R^{3b}$ are independently a hydrogen atom, a lower alkyl group, a lower alkyl-carbonyl group, or a phenyl group which may be substituted by a halogen atom or a halogeno-lower alkyl group; X is a carbon atom or a sulfur atom; Y is an oxygen atom or a nitrogen atom; and the symbol means a single bond or double bond, and $R^1$, $R^2$ and n are as defined in claim 1, or a pharmaceutically acceptable salt thereof.

8. A compound according to claim 7, wherein X is a carbon atom and Y is an oxygen atom.

9. A compound according to claim 7, wherein X is a sulfur atom and Y is a nitrogen atom.

10. A compound according to claim 7, wherein $R^1$ is a substituted or unsubstituted phenyl group, a substituted or unsubstituted naphthyl group or a benzothienyl group, said substituted phenyl group and substituted naphthyl group have each independently one to three substituents independently selected from a halogen atom, a methyl group, a methoxy group, a trifluoromethyl group and a hydroxy group.

11. A compound according to claim 10, wherein $R^2$ is isopropyl.

12. A compound which is independently selected from a following compounds:

N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-(methylethyl)-2-oxoethyl](3,5-dimethylisoxazol-4-yl)carboxamide;

N-[(1S)-2-((2S)-2-{N-[(1S)-3,3,3-trifluoro-1-(2-naphthylmethyl)-2-oxopropyl]carbamoyl}pyrrolidinyl)-1-(methylethyl)-2-oxoethyl](3,5-dimethylisoxazol-4-yl)carboxamide;

N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-ethyl-2-oxoethyl](3,5-dimethylisoxazol-4-yl)carboxamide;

N-[1-((1R)-1-methylpropyl)(1S)-2-((2S)-2-{N-[(1S)-1-(benzo[b]thiophen-3-ylmethyl)-3,3,3-trifluoro-2-oxopropyl]carbamoyl}pyrrolidinyl)-2-oxoethyl](3,5-dimethylisoxazol-4-yl)carboxamide;

N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-methyl-2-oxoethyl](3,5-dimethylisoxazol-4-yl)carboxamide; and N-[(1S)-2-((2S)-2-{N-[(1S)-1-(benzo[b]thiophen-3-ylmethyl)-3,3,3-trifluoro-2-oxopropyl]carbamoyl}pyrrolidinyl)-1-(methylethyl)-2-oxoethyl](4-methyl(1,2,3,-thiadiazol-5-yl))carboxamide.

13. A pharmaceutical composition, which comprises as an active ingredient the compound as set forth in claim 4 in admixture with a pharmaceutically acceptable carrier or diluent.

14. A chymase inhibitory agent which comprises as the active ingredient a compound as set forth in claim 4.

15. A chymase inhibitory agent which comprises as the active ingredient a compound as set forth in claim 12.

16. A vascular permeability inhibitory agent for inflammatory diseases which comprises as the active ingredient the compound as set forth claim 4.

17. A vascular permeability inhibitory agent for inflammatory diseases which comprises as the active ingredient the compound as set forth in claim 12.

18. A compound according to claim 8, wherein $R^1$ is a substituted or unsubstituted phenyl group, a substituted or unsubstituted naphthyl group or a benzothienyl group, said substituted phenyl group and substituted naphthyl group have each independently one to three substituents independently selected from a halogen atom, a methyl group, a methoxy group, a trifluoromethyl group and a hydroxy group.

19. A compound according to claim 9, wherein $R^1$ is a substituted or unsubstituted phenyl group, a substituted or unsubstituted naphthyl group or a benzothienyl group, said substituted phenyl group and substituted naphthyl group have each independently one to three substituents independently selected from a halogen atom, a methyl group, a methoxy group, a trifluoromethyl group and a hydroxy group.

20. A compound according to claim 18, wherein $R^2$ is isopropyl.

21. A compound according to claim 19, wherein $R^2$ is isopropyl.

22. A pharmaceutical composition, which comprises as an active ingredient the compound as set forth in claim 5 in admixture with a pharmaceutically acceptable carrier or diluent.

23. A pharmaceutical composition, which comprises as an active ingredient the compound as set forth in claim 6 in admixture with a pharmaceutically acceptable carrier or diluent.

24. A pharmaceutical composition, which comprises as an active ingredient the compound as set forth in claim 7 in admixture with a pharmaceutically acceptable carrier or diluent.

25. A pharmaceutical composition, which comprises as an active ingredient the compound as set forth in claim 8 in admixture with a pharmaceutically acceptable carrier or diluent.

26. A pharmaceutical composition, which comprises as an active ingredient the compound as set forth in claim 9 in admixture with a pharmaceutically acceptable carrier or diluent.

27. A pharmaceutical composition, which comprises as an active ingredient the compound as set forth in claim 10 in admixture with a pharmaceutically acceptable carrier or diluent.

28. A pharmaceutical composition, which comprises as an active ingredient the compound as set forth in claim 11 in admixture with a pharmaceutically acceptable carrier or diluent.

29. A pharmaceutical composition, which comprises as an active ingredient the compound as set forth in claim 12 in admixture with a pharmaceutically acceptable carrier or diluent.

30. A chymase inhibitory agent which comprises as the active ingredient a compound as set forth in claim 5.

31. A chymase inhibitory agent which comprises as the active ingredient a compound as set forth in claim 6.

32. A chymase inhibitory agent which comprises as the active ingredient a compound as set forth in claim 7.

33. A chymase inhibitory agent which comprises as the active ingredient a compound as set forth in claim 8.

34. A chymase inhibitory agent which comprises as the active ingredient a compound as set forth in claim 9.

35. A chymase inhibitory agent which comprises as the active ingredient a compound as set forth in claim 10.

36. A chymase inhibitory agent which comprises as the active ingredient a compound as set forth in claim 11.

37. A chymase inhibitory agent which comprises as the active ingredient a compound as set forth in claim 12.

38. A vascular permeability inhibitory agent for inflammatory diseases which comprises as the active ingredient the compound as set forth claim 5.

39. A vascular permeability inhibitory agent for inflammatory diseases which comprises as the active ingredient the compound as set forth claim 6.

40. A vascular permeability inhibitory agent for inflammatory diseases which comprises as the active ingredient the compound as set forth claim 7.

41. A vascular permeability inhibitory agent for inflammatory diseases which comprises as the active ingredient the compound as set forth claim 8.

42. A vascular permeability inhibitory agent for inflammatory diseases which comprises as the active ingredient the compound as set forth claim 9.

43. A vascular permeability inhibitory agent for inflammatory diseases which comprises as the active ingredient the compound as set forth claim 10.

44. A vascular permeability inhibitory agent for inflammatory diseases which comprises as the active ingredient the compound as set forth claim 11.

45. A vascular permeability inhibitory agent for inflammatory diseases which comprises as the active ingredient the compound as set forth claim 12.

* * * * *